US012758207B2

(12) United States Patent
Hart et al.

(10) Patent No.: US 12,758,207 B2
(45) Date of Patent: Oct. 13, 2026

(54) SURGICAL ACCESS DEVICE COMPRISING INTERNAL RETRACTOR

(71) Applicant: Applied Medical Resources Corporation, Rancho Santa Margarita, CA (US)

(72) Inventors: Charles C. Hart, Rancho Santa Margarita, CA (US); Gary M. Johnson, Rancho Santa Margarita, CA (US); Eric Nguyen, Lake Elsinore, CA (US); Edward D. Pingleton, San Juan Capistrano, CA (US); Kennii Pravongviengkham, Rancho Santa Margarita, CA (US); Ghassan Sakakine, Rancho Santa Margarita, CA (US); Serene Wachli, Rancho Santa Margarita, CA (US); John R. Brustad, Rancho Santa Margarita, CA (US); Olivia Tran, San Diego, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 18/968,489

(22) Filed: Dec. 4, 2024

(65) Prior Publication Data

US 2025/0169810 A1 May 29, 2025

Related U.S. Application Data

(63) Continuation of application No. 17/700,270, filed on Mar. 21, 2022, now Pat. No. 12,161,317, which is a (Continued)

(51) Int. Cl.
*A61B 17/02* (2006.01)
*A61B 17/00* (2006.01)
*A61B 17/34* (2006.01)

(52) U.S. Cl.
CPC ...... *A61B 17/0293* (2013.01); *A61B 17/3423* (2013.01); *A61B 2017/00265* (2013.01)

(58) Field of Classification Search
CPC ............ A61B 17/0293; A61B 17/3423; A61B 2017/00265; A61B 17/02; A61B 17/0281; A61B 2017/0287
See application file for complete search history.

(56) References Cited

U.S. PATENT DOCUMENTS 1,275,520 A 8/1918 Bell
1,947,649 A 2/1934 Kadavy (Continued)

FOREIGN PATENT DOCUMENTS

WO WO 91/14392 10/1991
WO WO 2007/002392 A2 1/2007

OTHER PUBLICATIONS

European Patent Office, Supplementary Partial European Search Report for European Patent Application No. 04703698.3 dated Jun. 23, 2008, entitled "Internal Tissue Retractor".

(Continued)

*Primary Examiner* — Eduardo C Robert
*Assistant Examiner* — Tara Rose E Carter
(74) *Attorney, Agent, or Firm* — Patrick Ikehara

(57) ABSTRACT

Devices, methods, and systems provide a surgical access device comprising an internal retractor device integrated with or coupled to a body wall or wound retractor. The wound retractor retracts an opening in a body wall into a body cavity, while the internal retractor permits a user to control the positions of internal structures within the body (Continued)

cavity, thereby permitting a user to define a surgical field. Embodiments of the internal retractor are adjustable.

14 Claims, 24 Drawing Sheets

Related U.S. Application Data continuation of application No. 16/580,469, filed on Sep. 24, 2019, now Pat. No. 11,278,271, which is a continuation of application No. 15/844,336, filed on Dec. 15, 2017, now Pat. No. 10,456,125, which is a continuation of application No. 13/909,669, filed on Jun. 4, 2013, now Pat. No. 9,867,604, which is a continuation of application No. 12/840,989, filed on Jul. 21, 2010, now Pat. No. 8,469,883.

(60) Provisional application No. 61/227,206, filed on Jul. 21, 2009.

(56) References Cited

U.S. PATENT DOCUMENTS

| | | | | |
|---|---|---|---|---|
| 3,882,855 | A | 5/1975 | Schulte et al. | |
| 4,190,042 | A | 2/1980 | Sinnreich | |
| 4,889,107 | A | 12/1989 | Kaufman | |
| 5,080,088 | A | 1/1992 | LeVahn | |
| 5,143,082 | A | 9/1992 | Kindberg et al. | |
| 5,342,385 | A * | 8/1994 | Norelli | A61B 17/02 604/104 |
| 5,370,650 | A | 12/1994 | Tovey et al. | |
| 5,439,476 | A | 8/1995 | Frantzides | |
| 5,582,577 | A | 12/1996 | Lund et al. | |
| 5,651,762 | A | 7/1997 | Bridges | |
| 5,656,012 | A | 8/1997 | Sienkiewicz | |
| 5,803,902 | A | 9/1998 | Sienkiewicz et al. | |
| 5,865,728 | A | 2/1999 | Moll et al. | |
| 5,947,895 | A | 9/1999 | Warner | |
| 6,033,426 | A | 3/2000 | Kaji | |
| 6,155,972 | A | 12/2000 | Nauertz et al. | |
| 6,264,604 | B1 | 7/2001 | Kieturakis et al. | |
| 6,293,906 | B1 | 9/2001 | Vanden Hoek et al. | |
| 6,416,459 | B1 | 7/2002 | Haindl | |
| 6,416,554 | B1 | 7/2002 | Alferness et al. | |
| 6,425,856 | B1 | 7/2002 | Shapland et al. | |
| 6,450,983 | B1 | 9/2002 | Rambo | |
| 6,482,146 | B1 | 11/2002 | Alferness et al. | |
| 6,945,932 | B1 | 9/2005 | Caldwell et al. | |
| 2002/0045800 | A1 | 4/2002 | Lau et al. | |
| 2002/0133055 | A1 | 9/2002 | Haindl | |
| 2004/0073090 | A1 | 4/2004 | Butler et al. | |
| 2005/0209510 | A1 | 9/2005 | Bonadio et al. | |
| 2005/0273132 | A1 | 12/2005 | Shuluzas et al. | |
| 2005/0288558 | A1 | 12/2005 | Ewers et al. | |
| 2006/0074278 | A1 | 4/2006 | Petit et al. | |
| 2006/0129165 | A1 * | 6/2006 | Edoga | A61B 17/3421 604/174 |
| 2006/0149137 | A1 | 7/2006 | Pingleton et al. | |
| 2006/0149306 | A1 | 7/2006 | Hart et al. | |
| 2007/0060939 | A1 | 3/2007 | Lancial et al. | |
| 2007/0088204 | A1 | 4/2007 | Albrecht et al. | |
| 2007/0151566 | A1 * | 7/2007 | Kahle | A61B 5/0507 128/856 |
| 2008/0051817 | A1 | 2/2008 | Leahy | |

OTHER PUBLICATIONS

The International Bureau of WIPO, International Preliminary Report on Patentability, for International Application No. PCT/US2010/042781, titled Surgical Access Device Comprising Internal Retractor dated Nov. 24, 2014.

European Patent Office, Extended European Search Report for European Patent Application No. EP 19179256.3, titled "Surgical Access Device Comprising Internal Retractor," dated Sep. 18, 2019, 11 pgs.

European Patent Office, Extended European Search Report for European Application No. EP 22205975.0, entitled "Surgical Access Device Comprising Internal Retractor Surgical Access Device Comprising Internal Retractor," dated Feb. 6, 2023, 6 pgs.

* cited by examiner

FIG. 13A
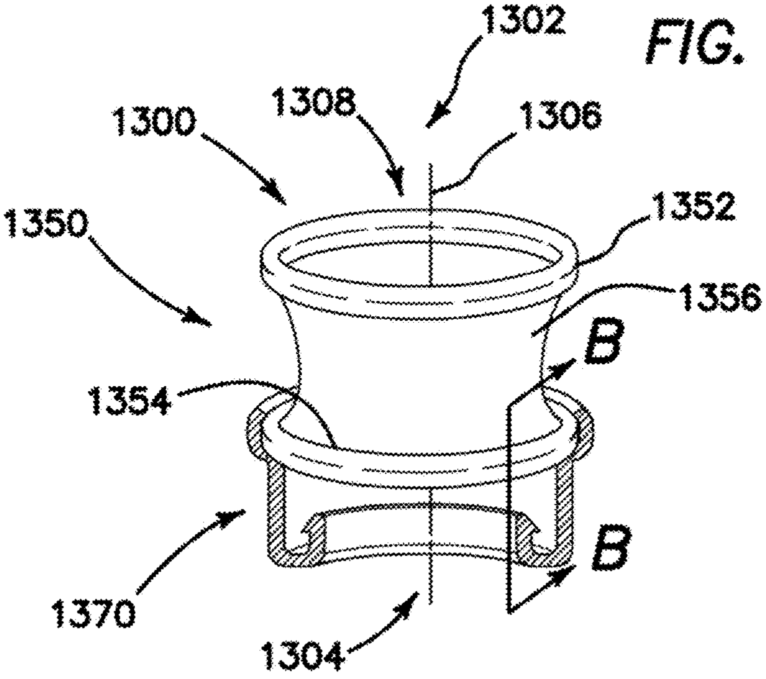
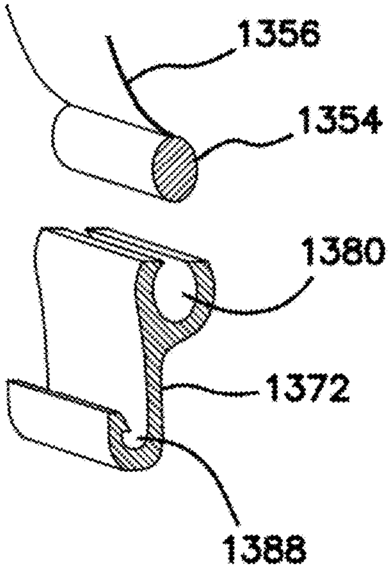
FIG. 13B
FIG. 13C
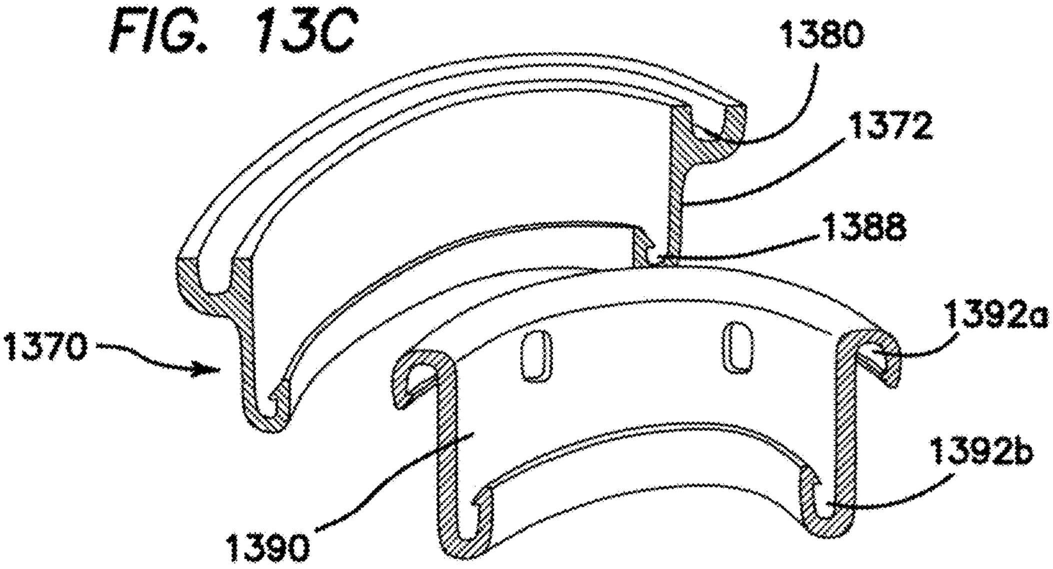

SURGICAL ACCESS DEVICE COMPRISING INTERNAL RETRACTOR

CROSS REFERENCE TO RELATED APPLICATION

This application claims is a continuation of U.S. application Ser. No. 17/700,270, filed Mar. 21, 2022, which a continuation of U.S. application Ser. No. 16/580,469, filed Sep. 24, 2019, which is now U.S. Pat. No. 11,278,271, which is a continuation of U.S. application Ser. No. 15/844,336, filed Dec. 15, 2017, which is now U.S. Pat. No. 10,456,125, which is a continuation of U.S. application Ser. No. 13/909,669, filed Jun. 4, 2013, which is now U.S. Pat. No. 9,867,604, which is a continuation of U.S. application Ser. No. 12/840,989, filed Jul. 21, 2010, which is now U.S. Pat. No. 8,469,883, which claims the benefit of U.S. Application No. 61/227,206, filed Jul. 21, 2009, the disclosures of which are incorporated by reference in their entirety.

BACKGROUND

Technical Field

The present disclosure is generally directed to surgical devices, and more specifically, to a surgical access device comprising a wound retractor and an internal retractor.

Description of the Related Art

Abdominal surgical procedures often entail entry into a patient's abdominal cavity and subsequent manipulation of internal structures therein, such as the small intestine, colon, mesentery, and other fatty structures. For example, large portions of a patient's small intestine are often displaced to provide clear access to the patient's spleen in some surgical procedures thereon. Gauze pads and/or sponges are often used to dam-up the displaced structures. Pads and/or sponges often slip and/or are difficult to place, however, especially through smaller incision sites. The pads and/or sponges are also typically carefully accounted for during surgery, thereby preventing one from being left behind within the patient.

Recent abdominal surgical procedures prefer smaller incisions, for example, laparoscopic surgeries. Laparoscopic surgical procedures often involve multiple small incisions of from between about five millimeters to about twelve millimeters. Some more complex procedures include a larger single incision. For instance, a five centimeter incision at the umbilicus that is circumferentially retracted by a circular wound retractor accommodates several laparoscopic instruments at the same time, or even a surgeon's hand extending into the abdominal cavity. Maintaining a clear operative area within the abdominal cavity while limiting the access area is desirable.

Additionally, surgical procedures of the lower abdomen and pelvis are also performed using single-incision techniques, in which a clear, unrestricted working space is also desirable.

SUMMARY OF THE INVENTION

Devices, methods, and systems provide a surgical access device comprising an internal retractor device integrated with or coupled to a body wall or wound retractor. The wound retractor retracts an opening in a body wall into a body cavity, while the internal retractor permits a user to control the positions of internal structures within the body cavity, thereby permitting a user to define a surgical field. Embodiments of the internal retractor are adjustable.

Some embodiments provide surgical access device comprising: a wound retractor comprising an outer ring, an inner ring, and a tubular sheath extending between the outer ring and the inner ring; and an internal retractor coupled to the wound retractor in an operative state of the surgical access device, the internal retractor comprising a deformable frame, wherein in the operative state, at least a portion of the internal retractor extends distally of the inner ring.

In some embodiments, the outer ring of the wound retractor is rotatable around an annular axis thereof, thereby permitting adjustment of an effective length of the tubular sheath between the inner ring and the outer ring.

In some embodiments, the internal retractor and the wound retractor are integrated. In some embodiments, the internal retractor is user coupled to the wound retractor in the operative state.

In some embodiments, the internal retractor further comprises a connection member, wherein the connection member couples the internal retractor to the wound retractor. In some embodiments, the internal retractor comprises at least one of a flexible cover and a dam portion. In some embodiments, the internal retractor comprises at least one window therethrough.

In some embodiments, the internal retractor defines a generally rectangular or nonrectangular shape. In some embodiments, defines a generally serpentine shape. In some embodiments, the frame comprises at least one of a lattice, a mesh, a solid sheet, and a perforated sheet.

Some embodiments further comprise a cover disposed over the frame.

In some embodiments, the internal retractor comprises a deformable, planar frame, a cover disposed over the frame, and a connection feature couplable to the wound retractor.

In some embodiments, the frame comprises a plastically deformable material. In some embodiments, the frame comprises an elastically deformable material.

BRIEF DESCRIPTION OF THE DRAWINGS

FIG. 13A is a side view of another embodiment of an access device comprising an internal retractor comprising a body couplable to a wound retractor. FIG. 13B is a detail of the internal retractor. FIG. 13C is a perspective view of the body illustrated in FIG. 13A and an extender couplable to the body.

Similar reference characters refer to similar features throughout.

DETAILED DESCRIPTION OF CERTAIN EMBODIMENTS

Figure 1A:
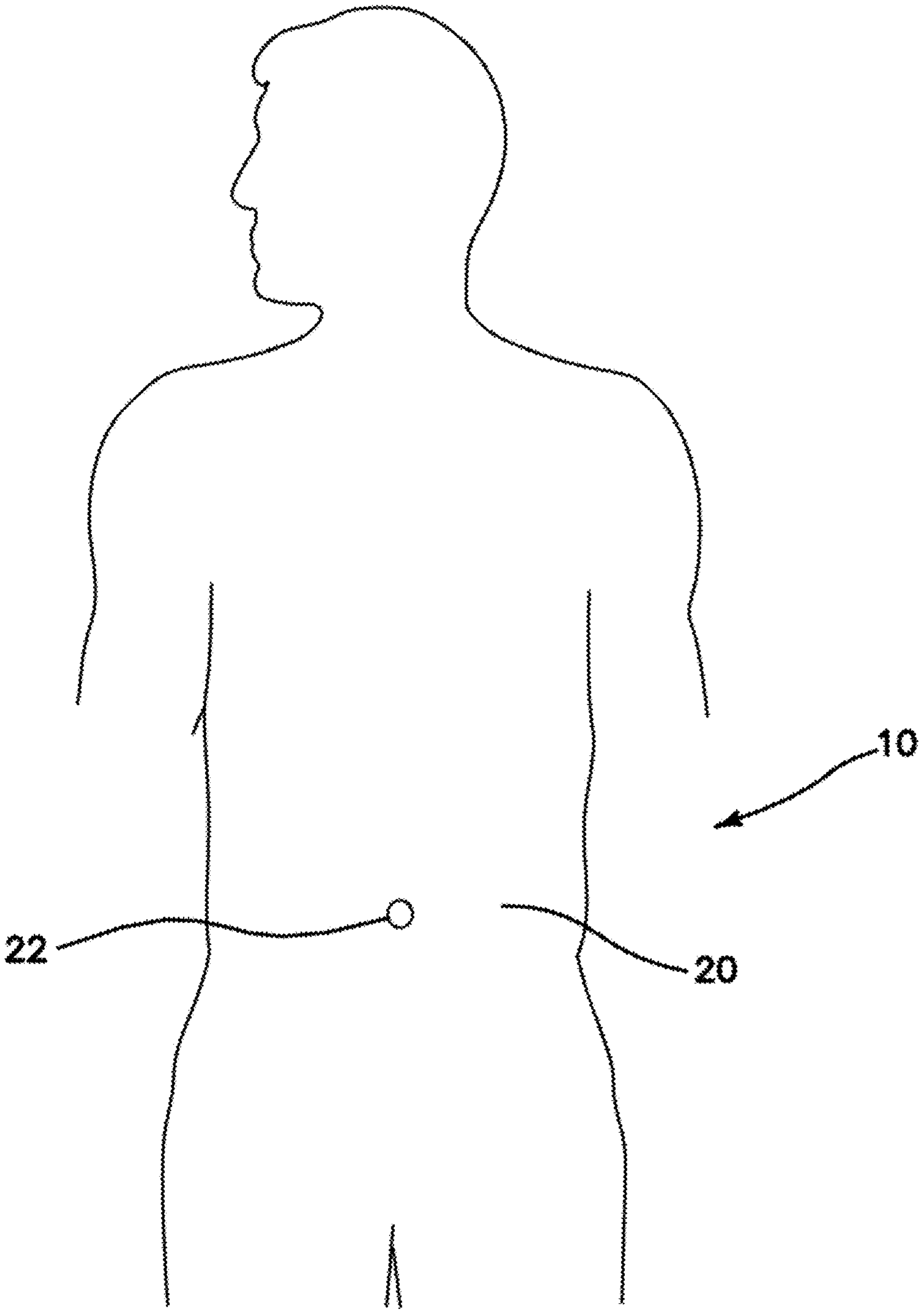
FIG. 1A is a front view of a patient for surgery of the abdomen.
Figure 1B:
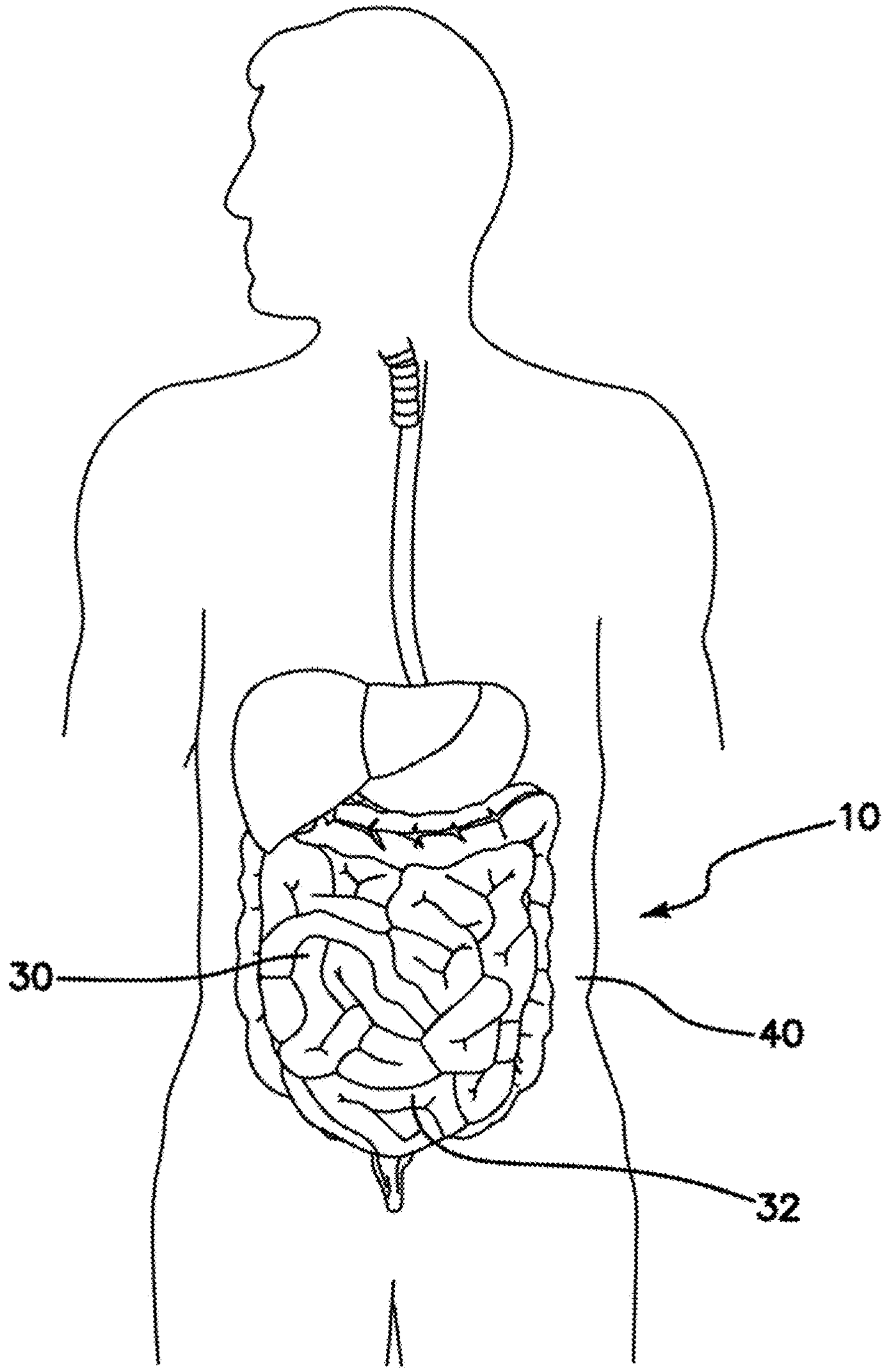
FIG. 1B is a partial front cross section illustrating abdominal content.
Figure 1C:
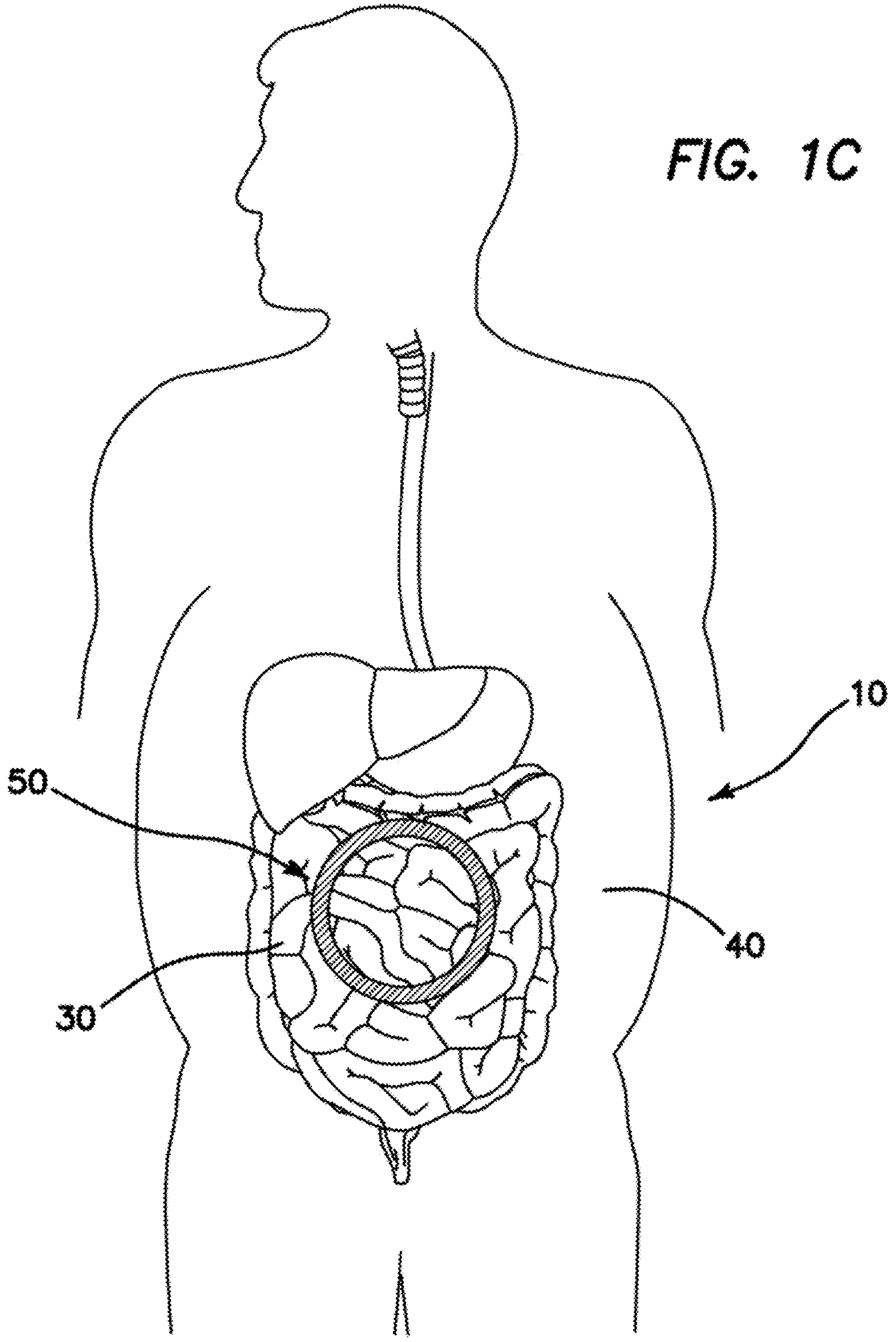
FIG. 1C is a partial front cross section of a patient schematically illustrating the placement of a wound retractor in the abdomen.
Figure 1D:
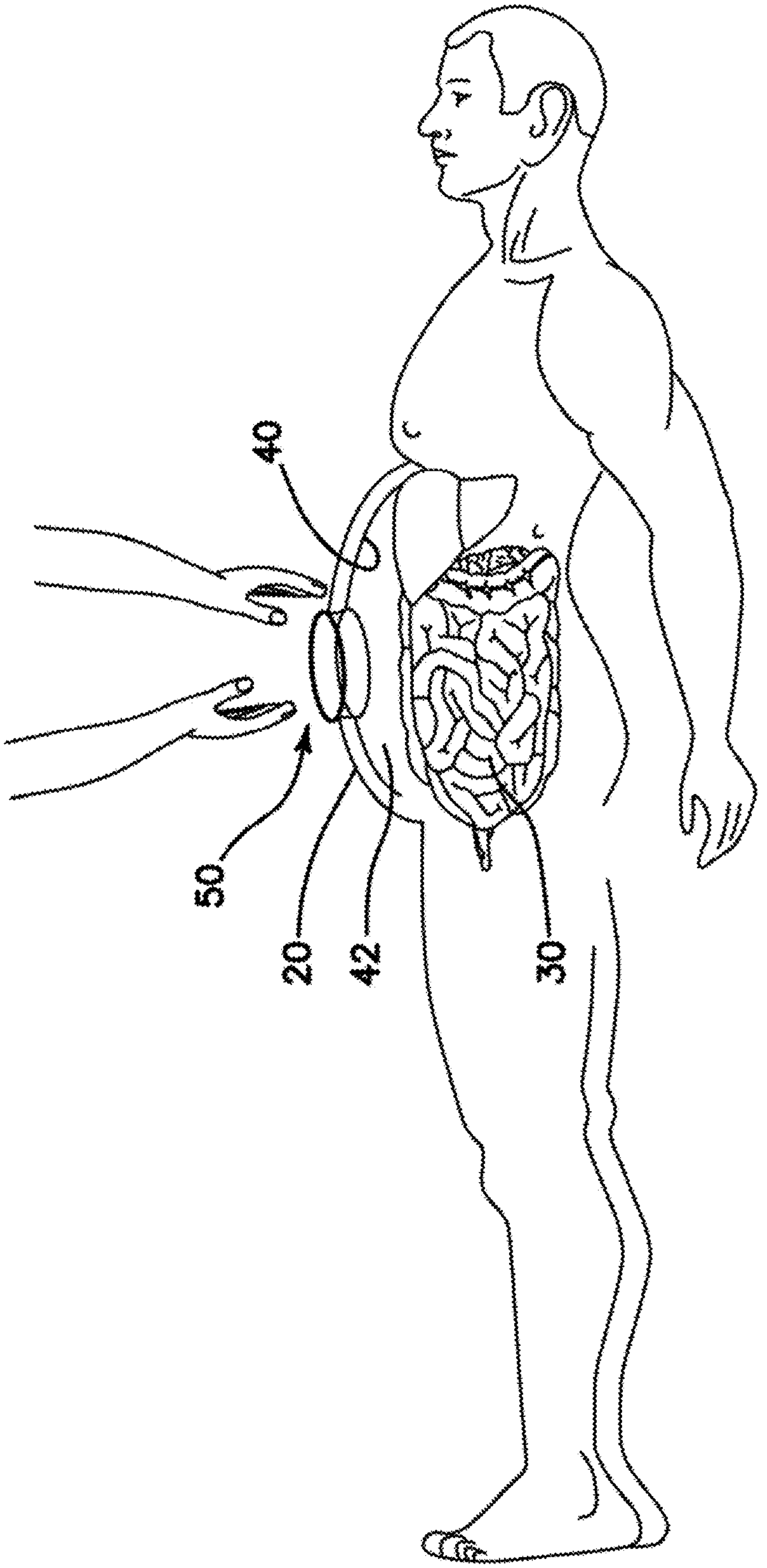
FIG. 1D is a partial side cross section of a patient illustrating the placement of a wound retractor in the abdomen.

FIG. 1A is a front view of a patient 10 for surgery of the abdomen 20 with an incision site 22 at the umbilicus. FIG. 1B is a partial cross section illustrating abdominal content 30 confined by a body wall 40, various adhesions, and connections. The content 30 is generally moist, slippery, and difficult to manage, and is especially true for the small intestine 32. As shown schematically in FIGS. 1C and 1*n* a partial side cross section in FIG. 1D, a circular retractor 50 is placed through an incision in the body wall 40 and into an abdominal cavity 42, thereby providing a surgeon with clear access to the abdominal content 30.

Figure 2:
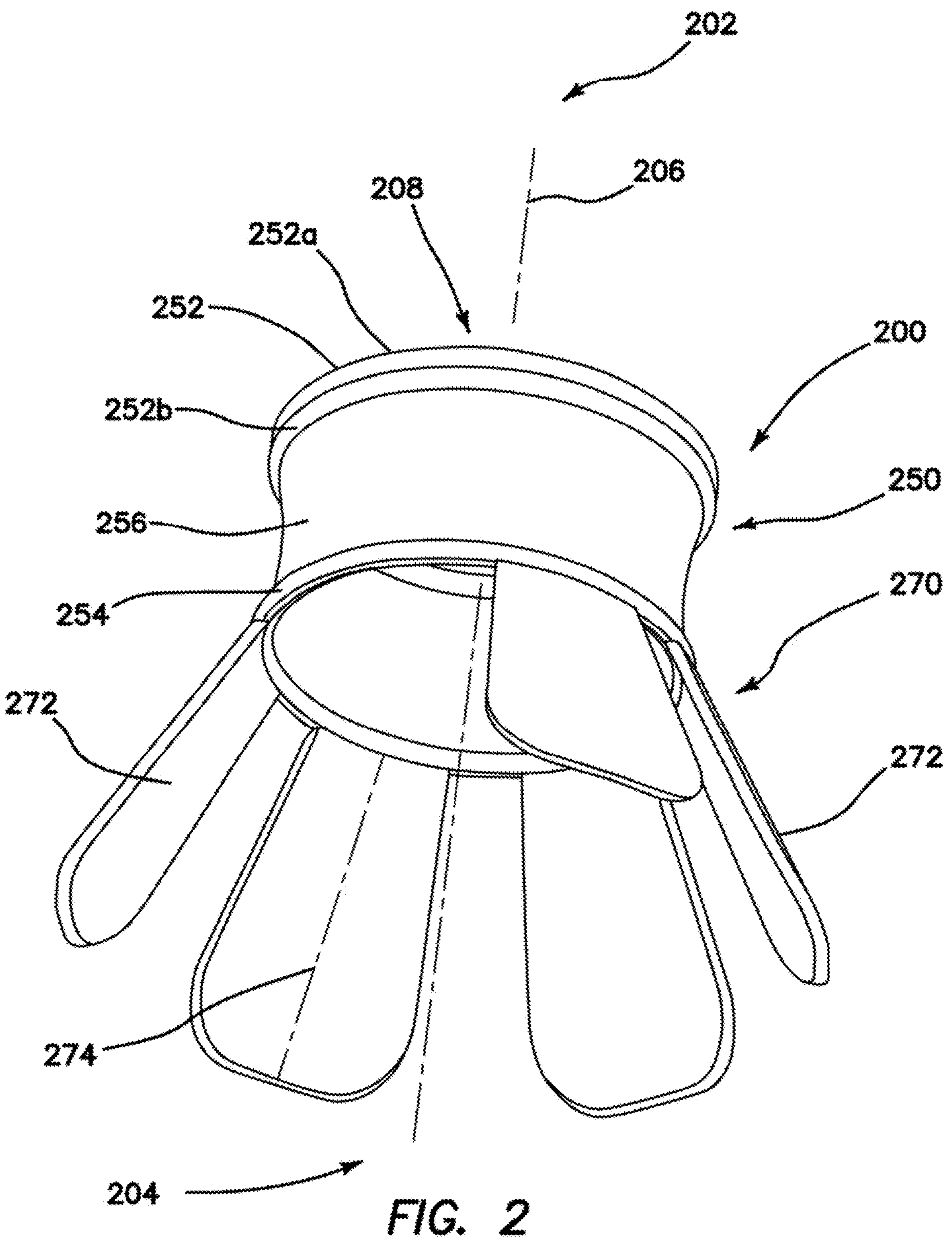
FIG. 2 is a perspective view of an embodiment of an access device comprising an internal retractor comprising a plurality of shapeable members.

FIG. 2 is a perspective view of an embodiment of a surgical access device 200 comprising a wound retractor 250 and an adjustable internal retractor 270. The wound retractor 250 is disposed at a proximal end 202 of the device 200, and the internal retractor 270 is disposed at a distal end 204. A longitudinal axis 206 extends from the proximal end 202 to the distal end 204. An access channel 208 extends through the device 200.

In the illustrated embodiment, the wound retractor 250 comprises a proximal or outer ring 252; a deformable distal or inner ring 254; and a flexible, tubular sheath 256 disposed between the outer ring 252 and the inner ring 254.

The inner ring 254 is deformable or flexible, which permits a user to insert the inner ring 254 through an incision or opening in a body wall with a smaller diameter than a relaxed diameter of the inner ring 254, and into a body cavity. The inner ring 254 is also sufficiently rigid to resist deformation when disposed against an inner surface of the body wall and under tension by the tubular sheath 256 extending through the incision or opening.

The wound retractor 250 is adjustable or non-adjustable. In the illustrated embodiment, the wound retractor 250 is an adjustable wound retractor. In the illustrated embodiment, the outer ring 252 is rotatable around an annular axis thereof, which winds and/or unwinds the tubular sheath 256 therearound, thereby adjusting an effective length of the tubular sheath 256 and a distance between the outer ring 252 and the inner ring 254. This adjustability permits a user to retract an opening or wound in a body cavity. The illustrated outer ring 252 comprises a first tube 252*a* and a second tube 252*b*. In other embodiments, the outer ring 252 has another shape, for example, comprising an oval, elliptical, and/or elongated cross section, with a major or longer axis either parallel with or perpendicular to the longitudinal 206. In some embodiments, the outer ring 252 further comprises one or more circumferential lumens. In some embodiments, a wire or hoop is disposed in one or more of the lumens. In some embodiments, the wire(s) or hoop(s) is non-compliant. In some embodiments, the wire(s) or hoop(s) is a split hoop.

The outer ring 252, inner ring 254, and tubular sheath 256 independently comprise any suitable biocompatible material, for example, one or more polymer resins. In embodiments in which the outer ring 252 comprises a wire or hoop, the wire or hoop comprise at least one of metal, stainless steel, spring steel, nitinol, polymer, ceramic, fibers, composites thereof, and the like.

In some embodiments, the retractor 250 is manufactured in a plurality of sizes, for example, diameters of at least one of the outer ring 252, the inner ring 256, and sheath 256, and/or length of the sheath 256. Some embodiments of the access device 200 further comprise a cap or lid (not illustrated) couplable to the outer ring 252, which closes and/or seals the access channel 208. Some embodiments of the cap or lid permit instrument and/or hand access through the cap or lid and into the access channel 208. Suitable wound retractors, caps, and lids are also disclosed in U.S. Pat. Nos. 7,727,146; 7,650,887; and 7,704,207, and U.S. Patent Application Publication No. 2010/0094227 A1, all the disclosures of which are incorporated by reference.

The internal retractor 270 in the illustrated embodiment is coupled to the inner ring 254 of the retractor 250 and extends distally of the inner ring 254. In the illustrated embodiment, the internal retractor 270 comprises a plurality of a plurality of elongate, shapeable members 272, each extending distally from the inner ring 254 of the wound retractor 250. In the illustrated embodiment, each shapeable member 272 angles away from the longitudinal axis 206, although in other embodiments, one or more of the shapeable members 272 extends in a different direction, for example, substantially parallel with the longitudinal axis 206 and/or towards the longitudinal axis 206.

Each shapeable member 272 in the illustrated embodiment comprises an elongate segment and/or wing that comprises any suitable material, for example, at least one of a polymer resin or metal. Some embodiments of the shapeable members 272 comprise an elastically deformable material, for example, metal, stainless steel, spring steel, polymer, fibers, and combinations thereof. Some embodiments of the shapeable members 272 comprise a malleable and/or plastically deformable material, for example, metal, stainless steel, a super elastic material, a shape memory material, clay, clay-like material, and combinations thereof. In some embodiments, one or more of the shapeable members 272 is partially or completely coated and/or covered with at least one of fabric, gauze, and foam thereby improving traction and/or fluid absorption. In some embodiments, one or more of the shapeable members 272 is partially or completely coated and/or covered with a fluid repellant and/or fluid impermeable material. In some embodiments, one or more of the shapeable members 272 comprises a textured and/or non-slip surface. Some embodiments of the shapeable members 272 comprise, for example, wire, strips, sheets, and perforated sheets.

In some embodiments one or more of the shapeable members 272 is curved along a transverse axis, thereby stiffening the shapeable members 272 using the principle that stiffens a Venetian blind slats. In the illustrated embodiment, at least one of an angle with the longitudinal axis 206, and a shape of each individual shapeable member 272 is adjustable, thereby retracting structures or organs from, and/or preventing structures or organs from entering a selected surgical field or area, thereby improving access to surgical targets therein. For example, in some embodiments, at least a portion of a shapeable member 272 is bendable transverse to a local longitudinal axis 274 thereof. In some embodiments, at least a portion of a shapeable member 272 is bendable or twistable around the local longitudinal axis 274.

In some embodiments, at least one of the shapeable members 272 is integrated with the inner ring 254. In some embodiments, at least one of the shapeable members 272 is separately manufactured, then coupled to the inner ring 254. For example, some embodiments of the inner ring 254 comprise at least one connecting feature to which the shapeable members 272 are coupled. In some embodiments, a proximal end of at least one shapeable member 272 comprises a connecting feature that secures the shapeable member 272 to the inner ring 254 at a desired angle with respect to the longitudinal axis 206. Suitable connecting features include, for example, mechanical fasteners, clips, clamps, friction fittings, hook-and-loop fasteners, snaps, ties, screws, latches, joints, hinges, ball joints, living hinges, and the like. In some embodiments, the shapeable members 272 are coupled to the inner ring 254 as a unit, for example, joined by a web and/or ring at a proximal end of the internal retractor 270. In some embodiments, shapeable members 272 are individually coupled to the inner ring 254. In some embodiments, one or more of the shapeable members 272 are removable as desired, for example, by cutting, breaking off, and the like. In some embodiments, the internal retainer 270 is removable, for example, after completing a portion of a surgical procedure. Some embodiments of the internal retractor 270 are not coupled to a wound retractor and are used independently of the wound retractor.

In the illustrated embodiment, the local axis 274 of each shapeable member 272 is substantially normal to the inner ring 254. In other embodiments, the local axis 274 of at least one shapeable member 272 subtends another angle with the inner ring 254 in a generally helical configuration. For example, in some embodiments, all of the shapeable members 272 together define a helical internal retractor 270.

Some embodiments of the internal retractor 270 further comprise a dam or cover (not illustrated) that is securable to one or more of the shapeable members 272, thereby defining an umbrella-like structure, which improves retraction of internal organs. The cover is similar to the dam portions described and illustrated below, and like the dam portions, comprises a single piece or a plurality of pieces, and similar materials. The cover is permanently or temporarily secured, for example, using adhesive, pressure sensitive adhesive, mechanical fasteners, clips, clamps, friction fittings, hook-and-loop fasteners, snaps, ties, screws, latches, and the like. In some embodiments, the cover comprises one or more pockets dimensioned to receive one or more of the shapeable members 272 therein. In some embodiments, one or more portions of the cover are removable by a user, for example, by cutting or tearing.

Figure 3:
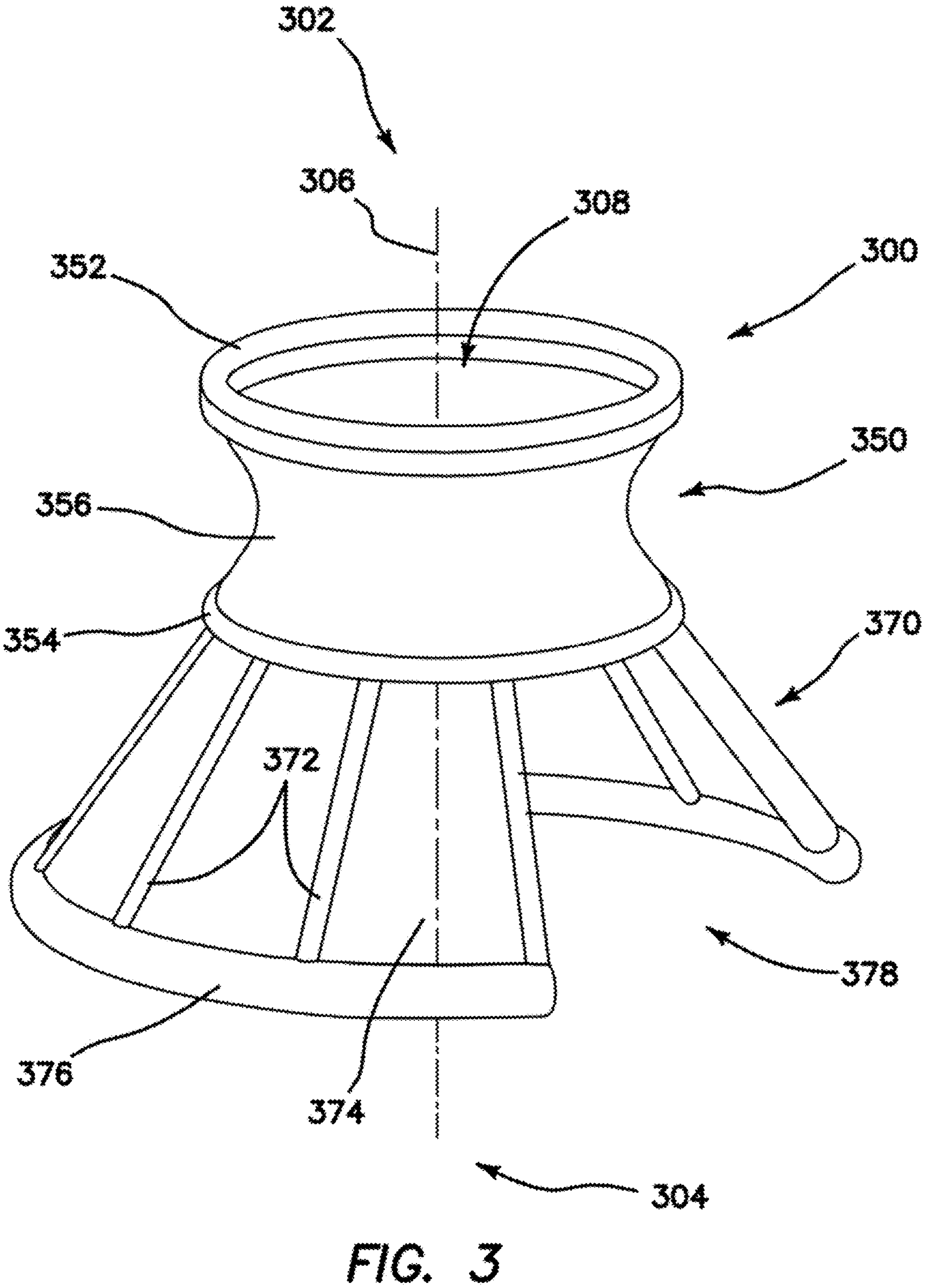
FIG. 3 is a perspective view of another embodiment of an access device comprising an internal retractor comprising an inflatable member.

FIG. 3 is a perspective view of an embodiment of a surgical access device 300 generally similar to the embodiment discussed above. The access device 300 comprises a proximal end 302, a distal end 304, a longitudinal axis 306, an access channel 308, a wound retractor 350 disposed at the proximal end 302, and an adjustable internal retractor 370 disposed at the distal end 304. The wound retractor 350 is generally similar to the embodiment of the wound retractor 250 described above, and comprises an outer ring 352, an inner ring 354, and a flexible sheath 356. The internal retractor 370 is integrated with the wound retractor 350 or manufactured as a separate component, which is preattached to the wound retractor 350 or user attached, or used without coupling to a wound retractor, as discussed above.

The illustrated embodiment of the internal retractor 370 comprises a plurality of longitudinally extending inflatable supporting members 372 and a plurality of dam portions 374 extending between adjacent supporting members 372. In other embodiments, a single dam portion 374 extends across a plurality of inflatable supporting members 372. The illustrated embodiment also comprises a peripheral ring 376. In some embodiments, the peripheral ring 376 is fluidly connected to at least one supporting member 372, and consequently, is inflatable with the at least one supporting member 372. In other embodiments, the peripheral ring 376 is not inflatable. In some embodiments, the peripheral ring 376 comprises a plurality of linked members, for example, ball-and-socket segments. In the illustrated embodiment, the internal retractor 370 is generally frustoconical in an inflated state, diverging distally from the longitudinal axis 304.

In the illustrated embodiment, the internal retractor 370 comprises an open area or window 378, which permits access to tissue and/or organs outside the perimeter of the internal retractor 370. The open area or window 378 allows a surgeon to place instruments and/or a hand into areas above, to the side of, and/or below the internal retractor 370, which is useful, for example, when working in the lower abdomen or pelvis. Some embodiments comprise a plurality of open areas or windows 378. Some embodiments of the internal retractor 370 do not comprise an open area or window. In some embodiments, the internal retractor 370 is supplied without an open area or window 378, and the user creates one or more as desired, for example, by removing selected dam portions 374. In some embodiments, the spacing of the supporting members 370 is not uniform, thereby permitting a user to select a desired size of the open area or window 378.

Embodiments of the internal retractor 370 comprise at least one of rubber, polymer resin, fabric, foam, and elastomer. In some embodiments, the supporting members 372, the dam portions 374, and the peripheral ring 376 comprise different materials. Some embodiments of the dam portions 374 comprise at least one of polymer, membrane, film, rubber, webbing, gauze, film, fabric, woven fabric, non-woven fabric, and knit fabric. In some embodiments, the dam portions 374 comprise an elastomeric or stretchable material, for example spandex. Some embodiments of the internal retractor 370 further comprise at least one flexible reinforcing member, for example, one or more ribs disposed on, through, or within at least one supporting member 372, dam portion 374, and/or the peripheral ring 376. In some embodiments, at least one supporting reinforcing member 372 is elastically deformable. In some embodiments, at least one supporting member 372 is plastically deformable. Suitable materials for the supporting member are described above. Suitable materials for the reinforcing members 372 include at least one of metal, a super elastic material, a shape memory material, polymer, fibers, and composites thereof. In some embodiments, the reinforcing members comprise at least one of wires, strips, bands, and the like.

In some embodiments, a retraction and/or retention force that the internal retractor 370 exerts on internal organs depends on the degree of inflation thereof. Consequently, the retraction and/or retention force is adjustable by the end user. Embodiments of the internal retractor are inflatable with gas, carbon dioxide, nitrogen, air, liquid, water, saline, Ringer's solution, isotonic solutions, and the like. In some embodiments, the inflation fluid is cooled and or heated as desired.

Figure 4:
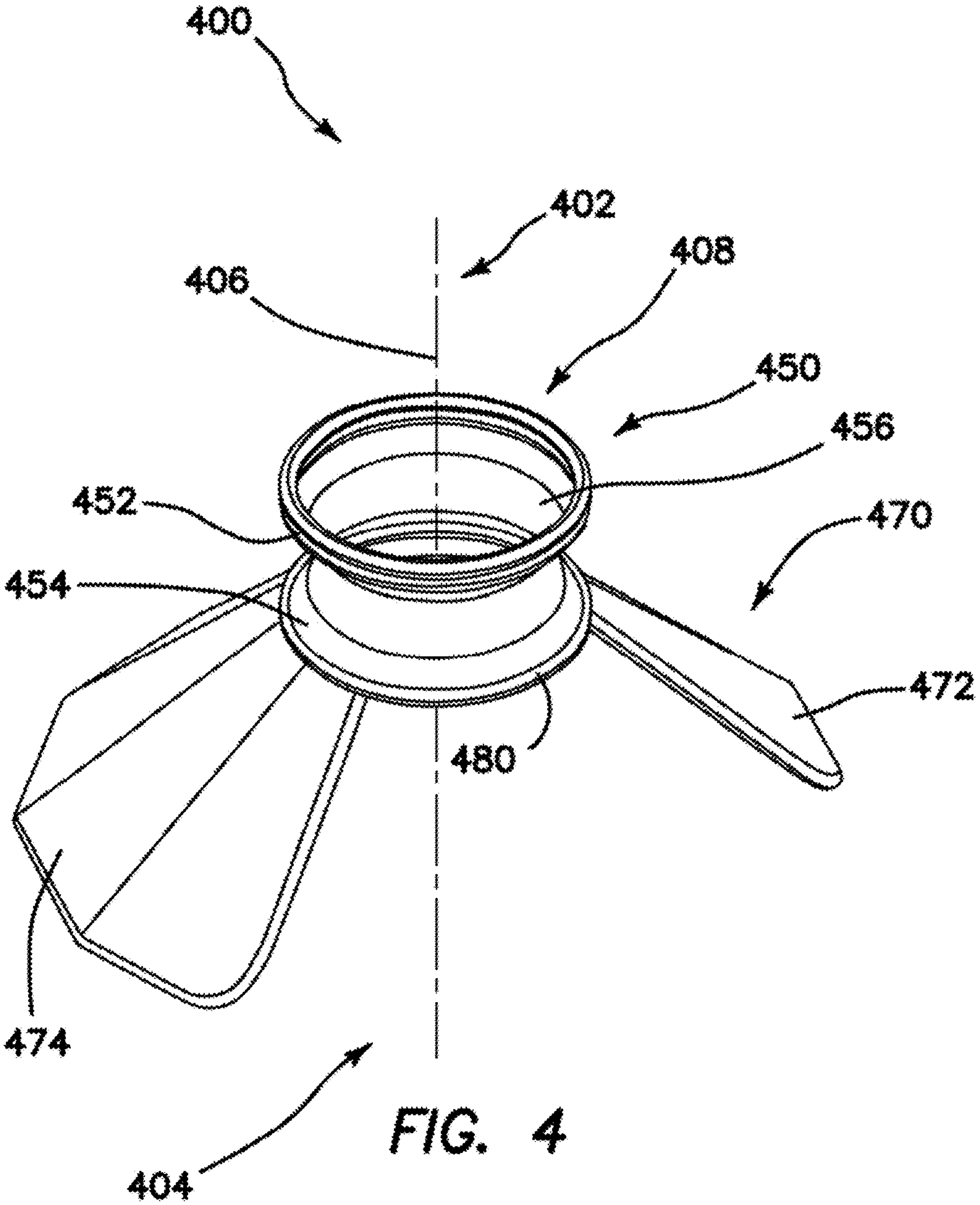
FIG. 4 is a perspective view of another embodiment of an access device comprising an internal retractor comprising a fan-like device.

FIG. 4 is a perspective view of another embodiment of a surgical access device 400 that is generally similar to the embodiments discussed above. The access device 400 comprises a longitudinal axis 406 extending from a proximal end 402 to a distal end 404, an access channel 408 extending through the device 400, a wound retractor 450 at the proximal end 402, and an adjustable internal retractor 470 at the distal end 404. The wound retractor 450 is generally similar to the embodiments of the wound retractor described above, and comprises an outer ring 452, an inner ring 454, and a flexible sheath 456. Embodiments of the internal retractor 470 are integrated, preattached, or user attached to the wound retractor 450, or used without coupling to a wound retractor, as discussed above.

In the illustrated embodiment, the internal retractor 470 comprises a plurality of individual segments 472 arrayed in a fan-like configuration. In the illustrated embodiment, each segment 472 angles away from the longitudinal axis 406. At least some of the segments 472 are slidably coupled to a hub 480, thereby defining an iris-like or folding-fan structure, there by allowing a user to adjust an opening or window 478 in the internal retractor as desired, thereby adjusting the degree of retention and/or retraction of internal organs. In the illustrated embodiment, the hub 480 comprises one or more tracks in which a proximal end of at least some segments 472 is slidably coupled. In some embodiments, the internal retainer 470 comprises a one-way mechanism that permits opening in one direction, only. In some embodiments, at least a portion of some of the segments 472 is malleable or plastically deformable. In the illustrated embodiment, a flexible cover or dam 474 similar to the cover or dam described above, is disposed over one or more of the segments 472.

Figure 5:
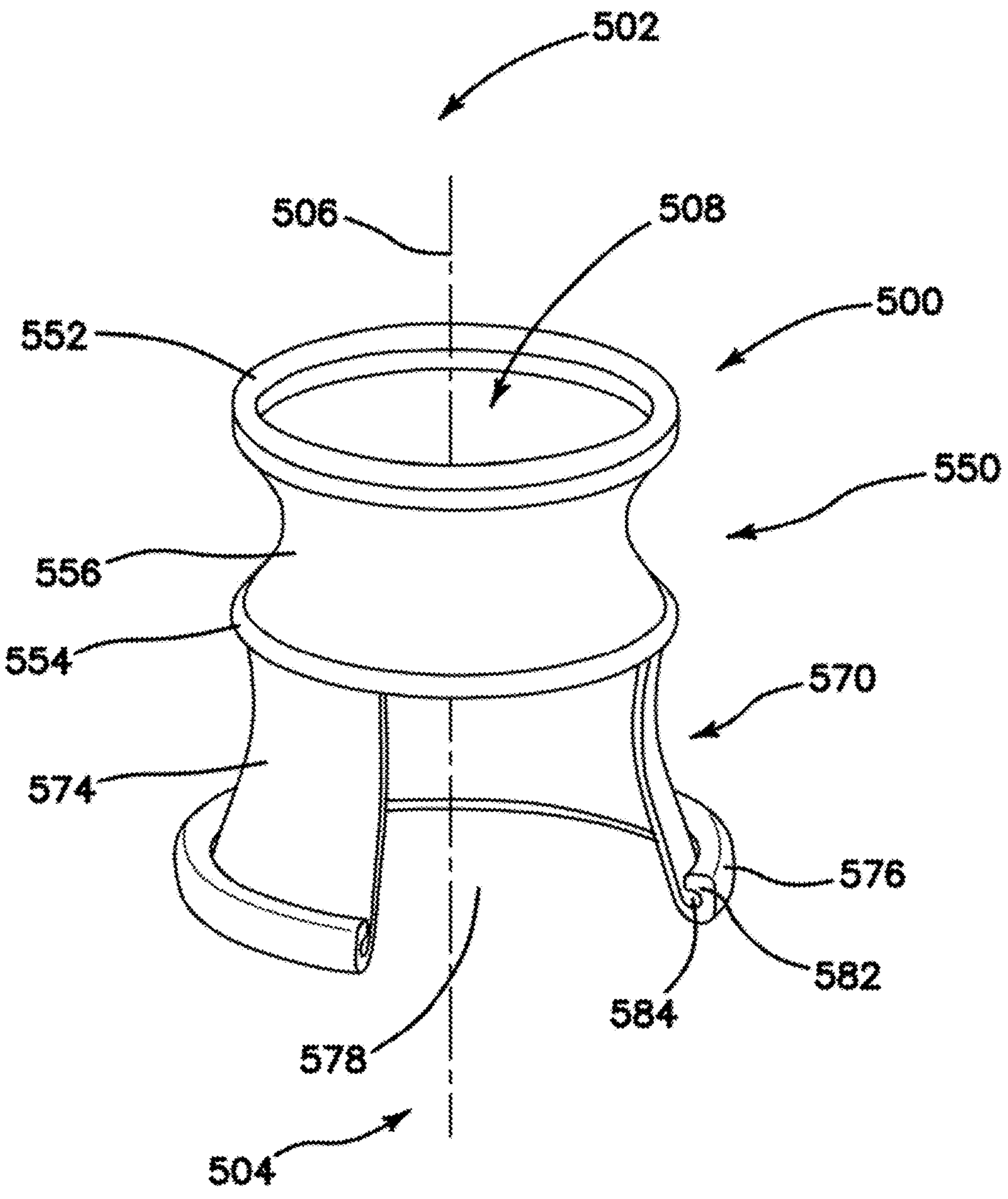
FIG. 5 is a perspective view of another embodiment of an access device comprising an internal retractor comprising a shapeable or deformable support member.

FIG. 5 illustrates in a perspective view another embodiment of a surgical access device 500 that is generally similar to the embodiments described above. The surgical access device 500 comprises a longitudinal axis 506 extending from a proximal end 502 to a distal end 504, an access channel 508 extending through the device 500, a wound retractor 550 disposed at the proximal end 502 and an internal retractor 570 disposed at the distal end 504. The wound retractor 550 is generally similar to the embodiments of the wound retractor described above, and comprises an outer ring 552, an inner ring 554, and a flexible sheath 556. Embodiments of the internal retractor 570 are integrated, preattached, or user attached to the wound retractor 550, or used without coupling to a wound retractor, as discussed above.

The internal retractor 570 comprises a distally extending skirt member 574 and a support member 576 coupled to a distal portion of the skirt member 574. Embodiments of the skirt member 574 comprise any material as discussed above for the cover or dam portion. Embodiments of the support member 576 comprise one or more of elastic, malleable, and/or plastically deformable portions, for example comprising one or more of the materials described above. In the illustrated embodiment, the support member 574 comprises an inwardly extending projection 582 defining and extending over an undercut or hollow portion 584, which provides the support member 574 with shape-memory characteristics. In other embodiments, the support member 574 comprises a plurality of linked members, for example, ball-and-socket segments.

The illustrated embodiment also comprises a window 578. In some embodiments, the window 578 is preformed. In others, the window 578 is user created. In the illustrated embodiment, the window 578 includes a gap in the support member 576. In other embodiments, the window 578 extends only through the skirt member 574 and does not comprise a gap in the support member 576.

Figure 6A:
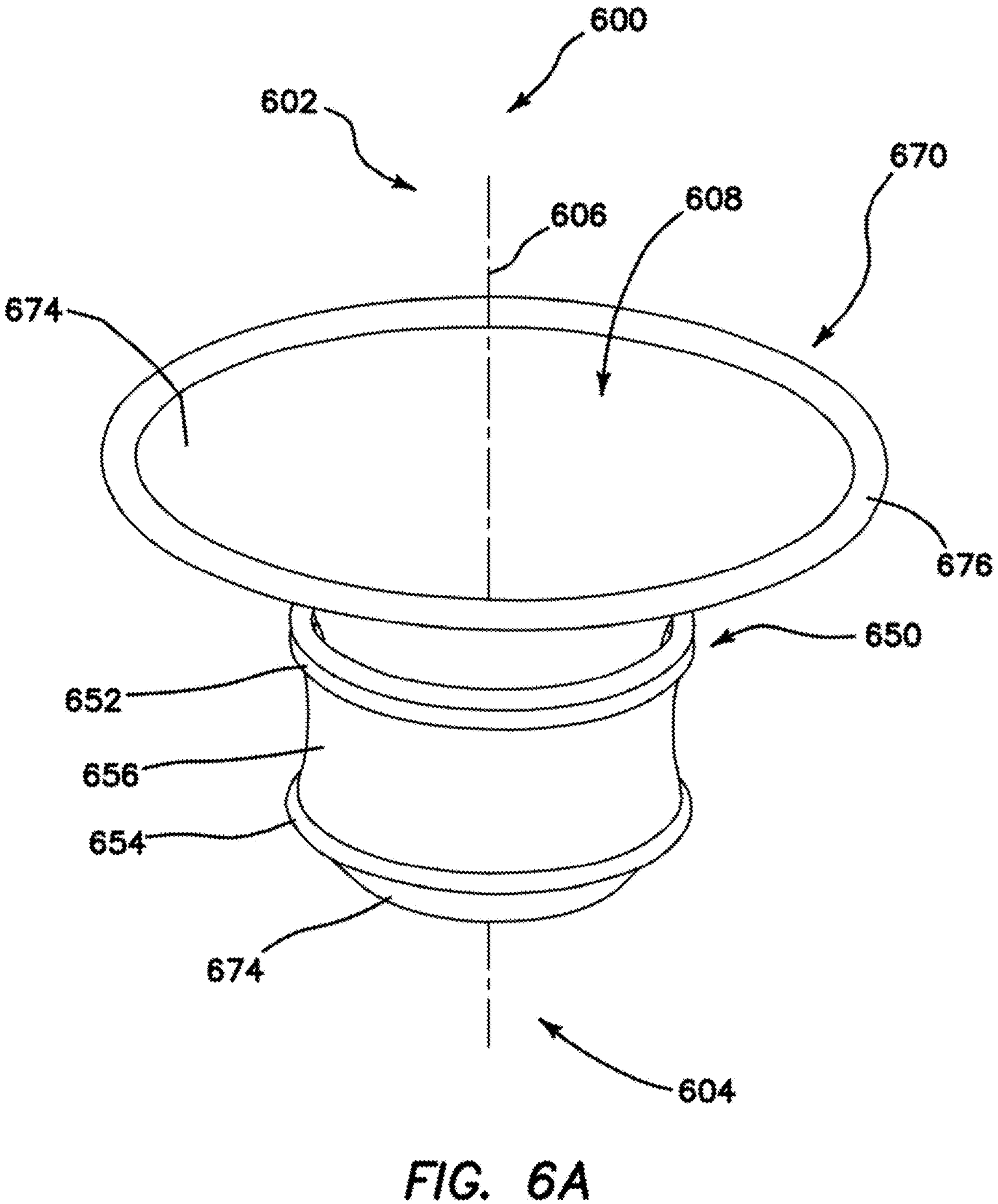
FIG. 6A is a perspective view of another embodiment of an access device comprising a shapeable internal structure in an undeployed configuration.

FIG. 6A is a perspective view of another embodiment of an access device 600 that is generally similar to the embodiments described above. The surgical access device 600 comprises a longitudinal axis 606 extending from a proximal end 602 to a distal end 604, an access channel 608 extending through the device 600, a wound retractor 650 disposed at the proximal end 602 and an internal retractor 670. The wound retractor 650 is generally similar to the embodiments of the wound retractor described above, and comprises an outer ring 652, an inner ring 654, and a flexible sheath 656. Embodiments of the internal retractor 670 are integrated, preattached, or user attached to the wound retractor 650, or used without coupling to a wound retractor, as discussed above.

The internal retractor comprises a tubular skirt 674 coupled to the wound retractor 650 and a retention ring 676 coupled to the free end of the skirt 674. In the illustrated embodiment, a diameter of the retention ring 676 is larger than a diameter of the outer ring 652 or the inner ring 654. In the illustrated embodiment, the tubular skirt 674 is coupled to the distal end of the wound retractor 650, for example, the inner ring 654. In other embodiments, the tubular skirt 674 is coupled to the proximal end of the of the wound retractor 650, for example, the outer ring 652. The skirt 674 comprises any suitable flexible material, for example, the materials described above for the cover or dam portion. The retention ring 676 comprises a malleable, deformable, shapeable, plastically deformable, and/or elastically deformable material, for example any of the materials described above. Some embodiments of the retention ring 676 comprise an internal malleable or plastically deformable spine. Some embodiments comprise a plurality of linked members, for example, ball-and-socket segments. Consequently, some embodiments of the retention ring are shapeable in a plane or in all directions.

The illustrated embodiment of the internal retractor 670 does not comprise a window. In some embodiments, one or more windows are preformed in the skirt 674. In some embodiments, a user creates windows in the skirt 674 as desired.

Figure 6B:
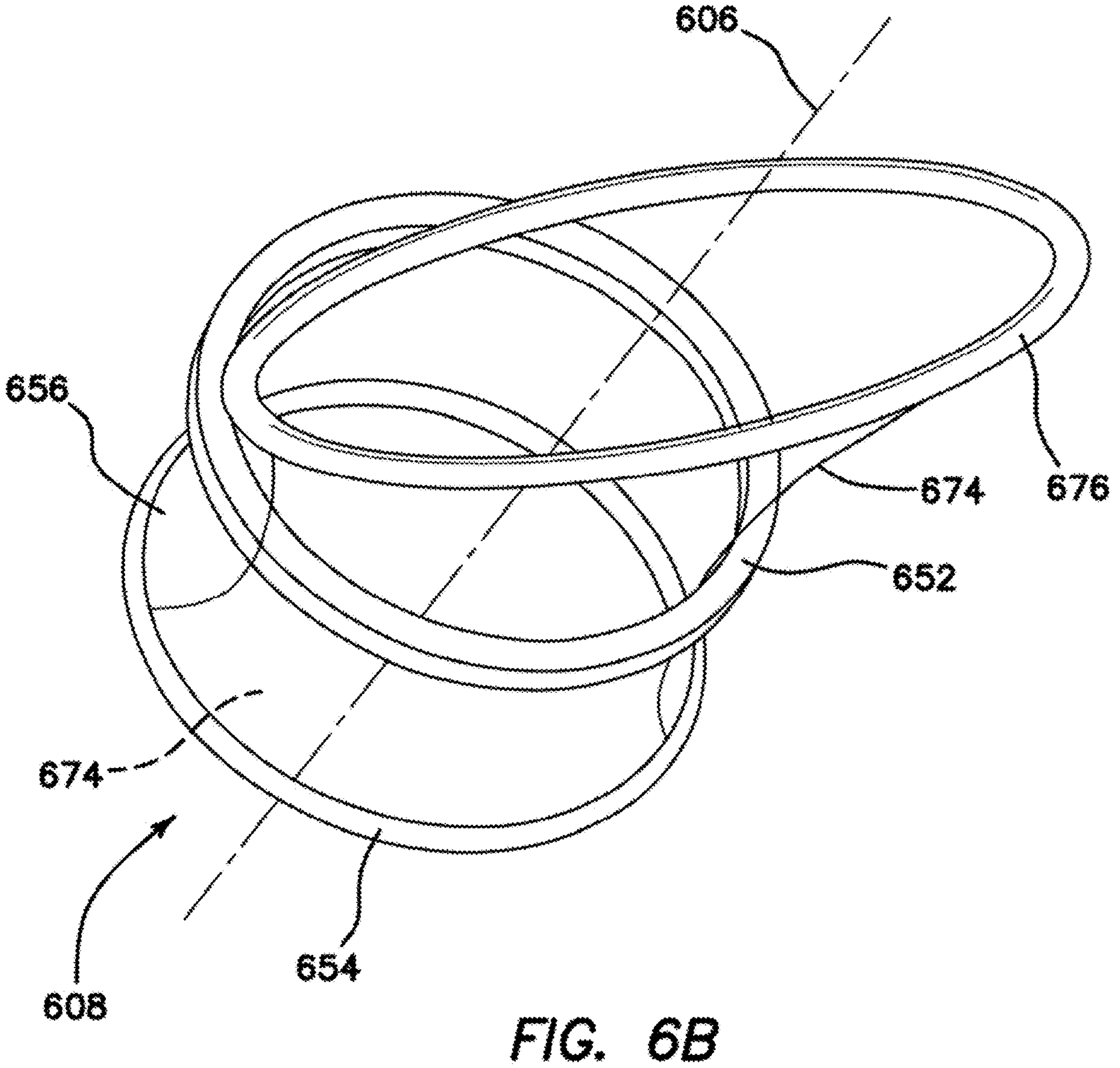
FIGS. 6B and 6C are perspective views of the access device illustrated in FIG. 6A in partially deployed configurations.
Figure 6C:
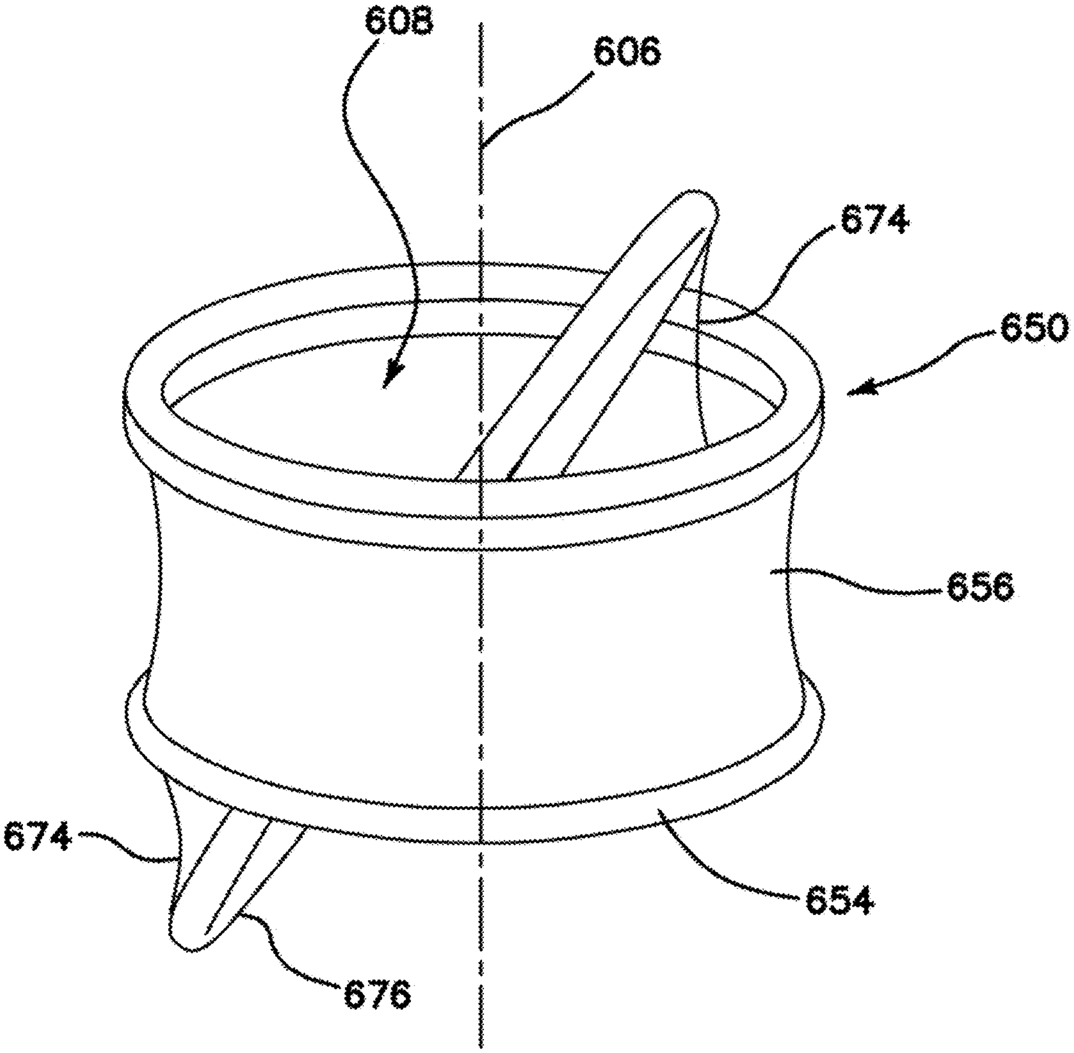
Figure 6D:
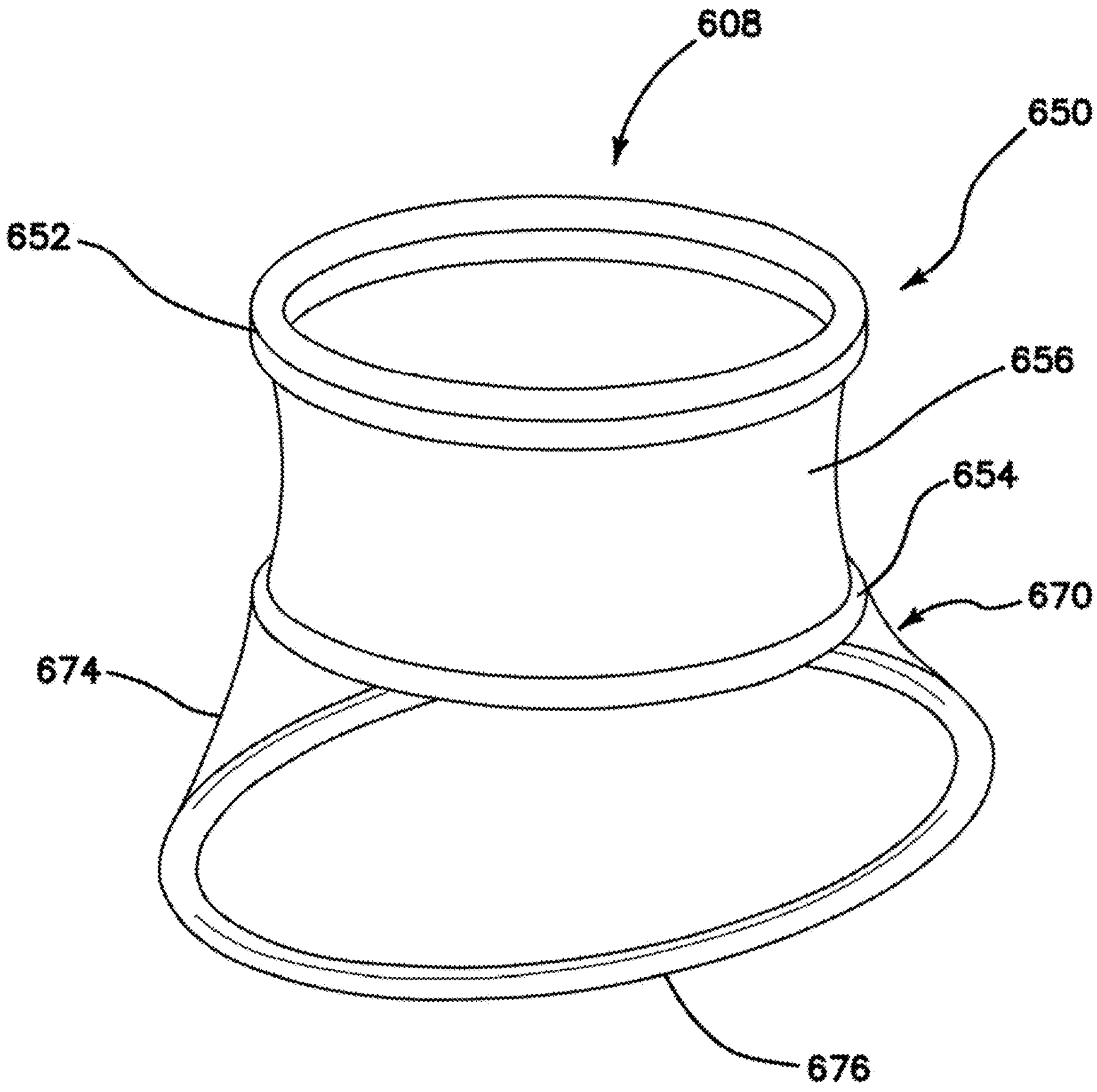
FIG. 6D is a perspective view of the access device illustrated in FIG. 6A in a deployed configuration.

The internal retractor 670 is illustrated in an undeployed state in FIG. 6A with the retention ring 676 is disposed proximally of the outer ring 652 of the wound retractor 650, with the skirt 674 extending through the access channel 608. FIGS. 6B-6C illustrate a intermediate states in converting the internal retractor 670 from the undeployed state or configuration illustrated in FIG. 6A, to a deployed state or configuration illustrated in FIG. 6D in which the retention ring 676 is distal of the inner ring 654. In the illustrated method, the retention ring 676 is passed through the access channel 606 through the wound retractor 650. In the conversion process, the large-diameter retention ring 676 is squeezed, twisted, and/or otherwise deformed to a size that fits through the access channel 608. In the deployed state or configuration illustrated in FIG. 6D, the large-diameter retention ring 676 is shaped and/or adjusted to retract the internal organs from a desired area in the body cavity. For example, in some embodiments, the retention ring 676 is nested beneath internal structures 30 (FIGS. 1B-1D), where the weight of the structures 30 secures the retention ring 676 in place.

Figure 7:
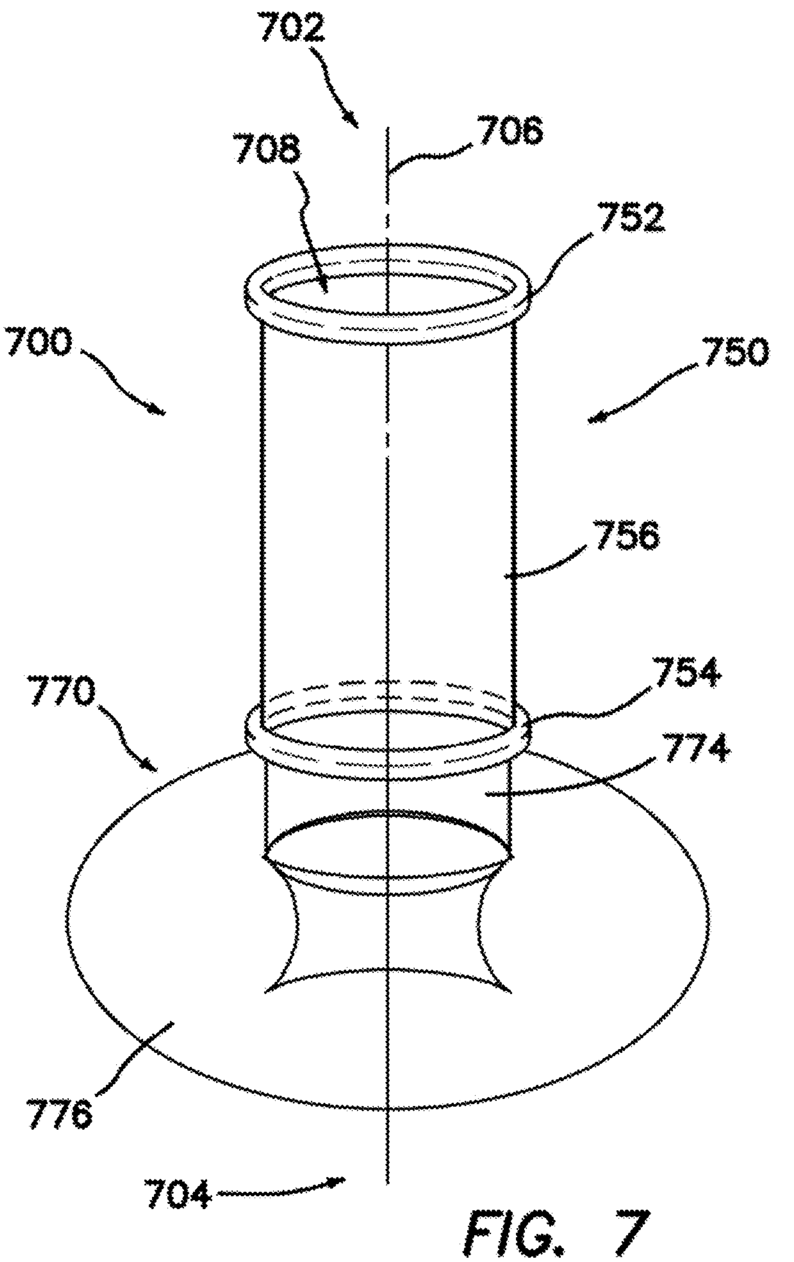
FIG. 7 is a perspective view of another embodiment of an access device comprising an internal retractor comprising an inflatable, toroidal internal retractor.

FIG. 7 illustrates in perspective view another embodiment of a surgical access device 700 that is generally similar to the embodiments described above. The surgical access device 700 comprises a longitudinal axis 706 extending from a proximal end 702 to a distal end 704, an access channel 708 extending through the device 700, a wound retractor 750 disposed at the proximal end 702 and an internal retractor 770. The wound retractor 750 is generally similar to the embodiments of the wound retractor described above, and comprises an outer ring 752, an inner ring 754, and a flexible sheath 756. Embodiments of the internal retractor 770 are integrated, preattached, or user attached to the wound retractor 750, or used without coupling to a wound retractor, as discussed above.

In the illustrated embodiment, the internal retractor 770 comprises a proximal, short tubular skirt 774 coupled to a distal, inflatable torus 776. Some embodiments of the internal retractor 770 do not comprise a skirt. In the undeployed state, the torus 776 is uninflated, while in the deployed state, the torus 776 is selectively inflated. Some embodiments of the skirt 774 and/or torus 776 comprise stiffening or reinforcing members.

Figure 8:
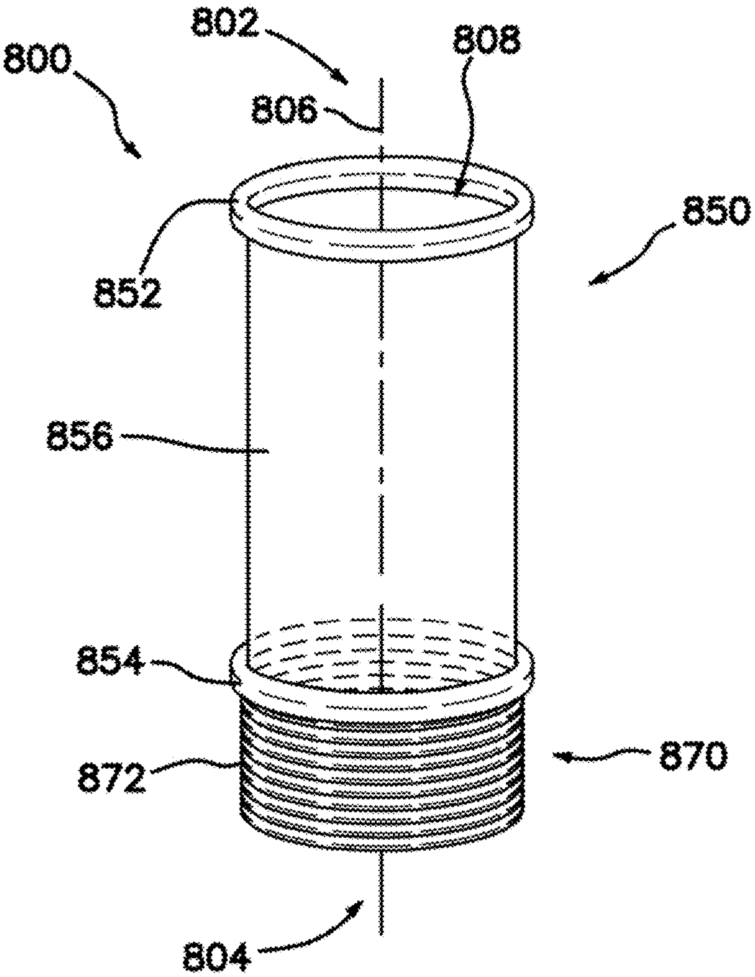
FIG. 8 is a perspective view of another embodiment of an access device comprising an internal retractor comprising a radially compressible tube.

FIG. 8 is a perspective view of another embodiment of an access device 800 that is generally similar to the embodiments described above. The surgical access device 800 comprises a longitudinal axis 806 extending from a proximal end 802 to a distal end 804, an access channel 808 extending through the device 800, a wound retractor 850 disposed at the proximal end 802 and an internal retractor 870. The wound retractor 850 is generally similar to the embodiments of the wound retractor described above, and comprises an outer ring 852, an inner ring 854, and a flexible sheath 856. Embodiments of the internal retractor 870 are integrated, preattached, or user attached to the wound retractor 850, or used without coupling to a wound retractor, as discussed above.

In the illustrated embodiment, the internal retractor 870 comprises a generally hollow cylinder or tube with open ends through which the access channel extends. In other embodiments, the internal retractor 870 has another shape, for example, an elliptical cylinder, or frustoconical with the larger end distal or with the smaller end distal. Embodiments of the internal retractor 870 are manufactured in a range of diameters and/or lengths. The internal retractor 870 is elastically deformable or plastically deformable. In some embodiments, one or more portions of the internal retractor 870 are elastically deformable and one or more portions are plastically deformable. Plastically deformable portions permit a user to shape the internal retractor 870 as desired. The internal retractor 870 is sufficiently deformable radially to permit insertion through an incision and/or the wound retractor 850.

In the illustrated embodiment, the internal retractor 870 comprises a plurality of stacked, annular segments 872. In the illustrated embodiment, the annular segments 872 are toroidal; however, in other embodiments, the annular segments have other shapes and/or a mixture of shapes. In some embodiments, the annular segments are detachable or separable from each other, for example, by cutting or tearing, which permits a user to adjust a length of the internal retractor. Some embodiments of the internal retractor 870 are separable longitudinally, for example, using one or more partial or complete longitudinal cuts, which permits a user to generate openings or windows as desired. Some embodiments of the internal retractor 870 further comprise a complete or partial cover, as discussed above.

In some embodiments, the internal retractor 870 is coupled to the wound retractor 850 such that the internal retractor 870 is translatable, thereby permitting the user to isolate a surgical field that is not directly below the wound retractor 850. In use, the wound retractor 850 is well anchored to a patient, thereby anchoring the internal retractor 870. Suitable coupling devices are known in the art, for example, rods, bars, clamps, clips, swivels, hinges, and the like. In some embodiments, the internal retractor 870 is not coupled to the wound retractor 850.

Figure 9:
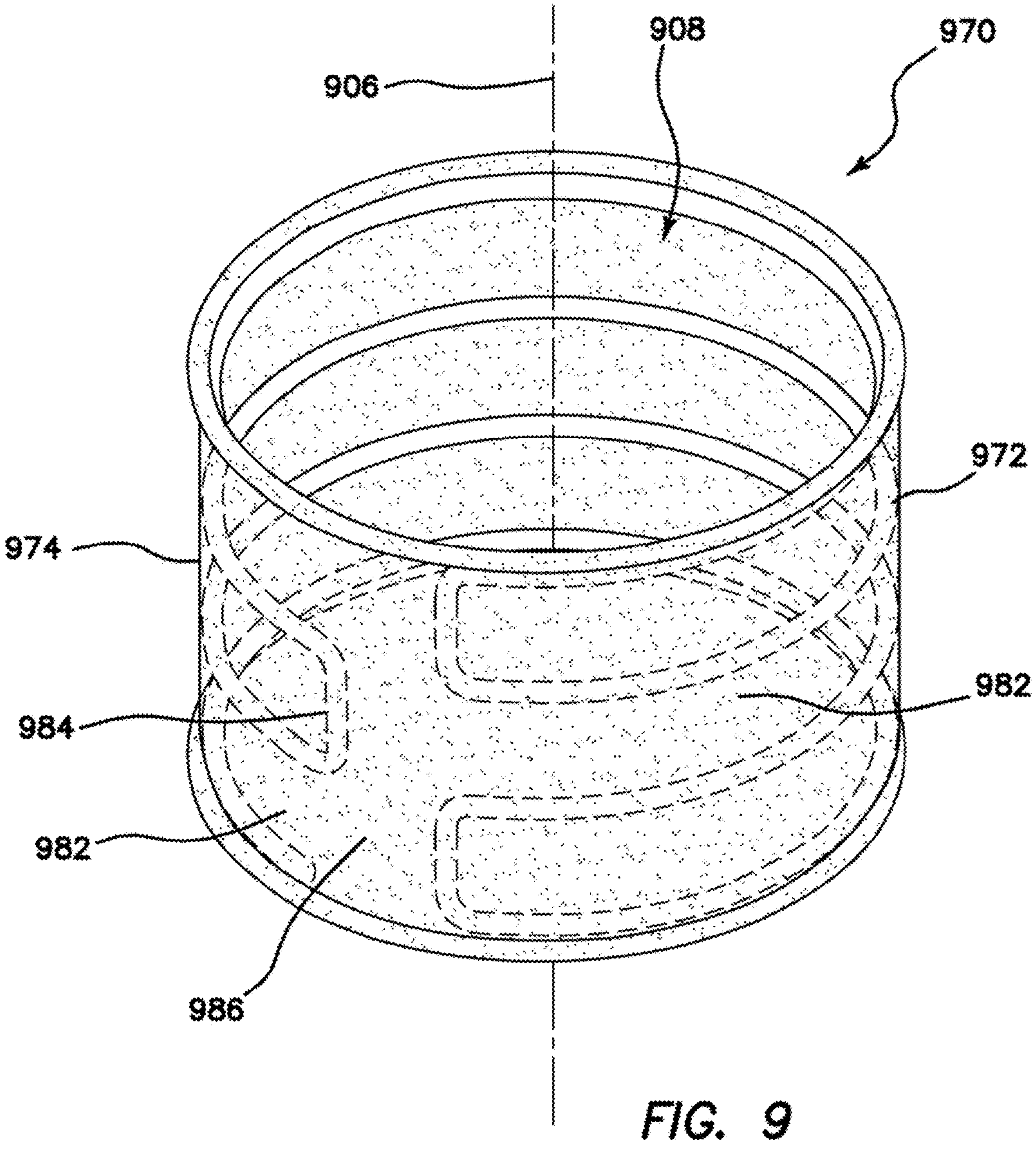
FIG. 9 is a perspective view of another embodiment of an access device comprising an internal retractor comprising a circumferentially serpentine frame defining a tube.

FIG. 9 is a perspective view of another embodiment of an internal retractor 970, which is similar to the embodiments described above. The internal retractor 970 is integrated with, couplable with, used with, or used independently of a wound retractor, as discussed above. The illustrated embodiment of the internal retractor 970 comprises a longitudinal axis 906, an access channel 908, and a serpentine frame 972 defining a hollow cylinder or tube. In other embodiments, the frame 972 defines a different shape, for example, frustoconical or an elliptical cylinder. The serpentine frame 972 defines a plurality of circumferential voids or openings 982 in the cylindrical surface into which circumferential fingers 984 defined by the frame 972 interleave when the frame 972 is compressed radially, for example, when inserting the internal retractor 970. Those skilled in the art will understand that in other embodiments, the serpentine frame 972 has a different shape that defines voids 982 and fingers 984 with different shapes. The frame 972 comprises a plastically deformable material, an elastically deformable material, or a combination thereof. In embodiments comprising a plastically deformable material, the internal retractor 970 is reshapeable or adjustable on deployment.

In the illustrated embodiment, the internal retractor 970 further comprises a cover or dam portion 974, as discussed above. In some embodiments, the cover is cuttable through a void area 986, which permits further adjustment in the deployed state. Other embodiments do not comprise a cover or dam portion.

Figure 10A:
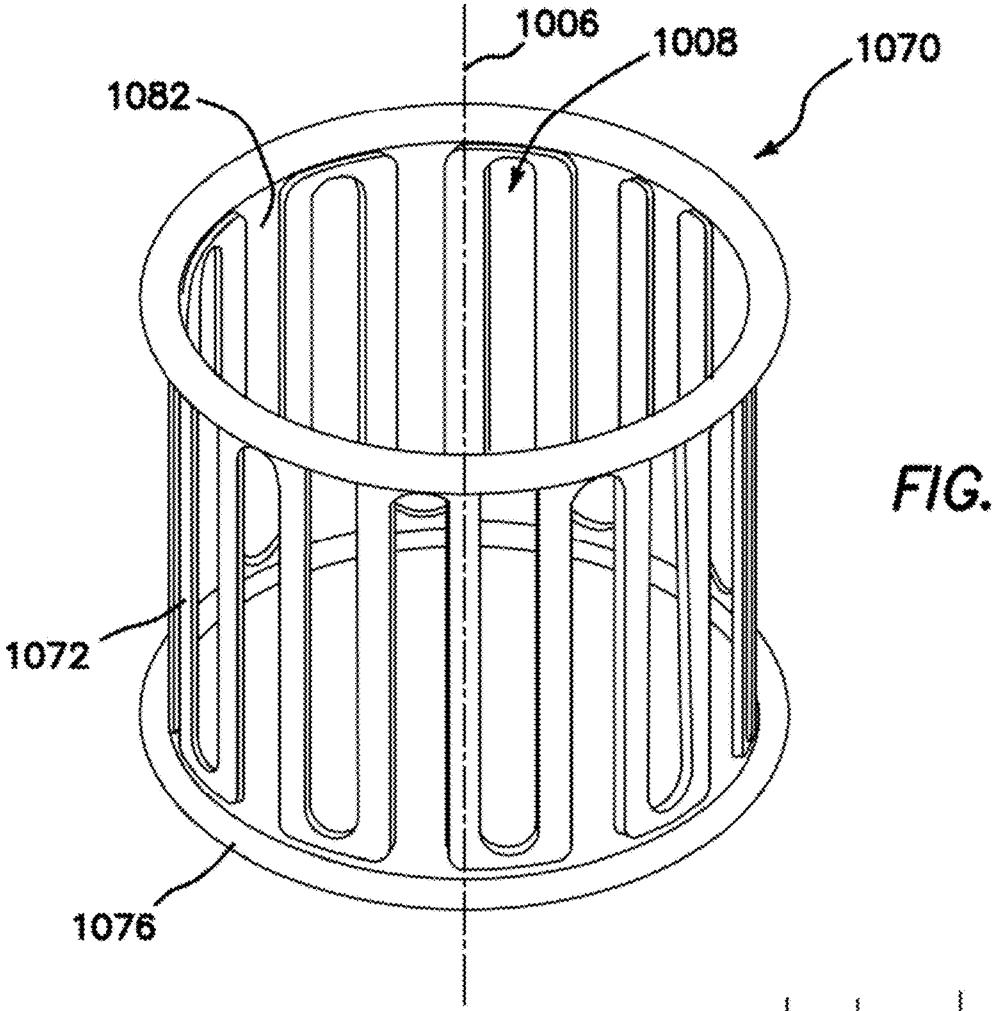
FIG. 10A is a perspective view of another embodiment of an internal retractor comprising a longitudinally serpentine frame defining a tube.

FIG. 10A is a perspective view of another embodiment of an internal retractor 1070, which is similar to the embodiments described above. The internal retractor 1070 is integrated with, couplable with, used with, or used independently of a wound retractor, as discussed above. The illustrated embodiment of the internal retractor 1070 comprises a longitudinal axis 1006, an access channel 1008, and a serpentine frame 1072 defining a hollow cylinder or tube. In other embodiments, the frame 1072 defines a different shape, for example, frustoconical or an elliptical cylinder. The serpentine frame 1072 defines a plurality of longitudinal voids or openings 1082 in the cylindrical surface, which permit a user to compress the frame 1072 radially, for example, when inserting the internal retractor 1070. Those skilled in the art will understand that in other embodiments, the frame 1072 comprises a plurality of longitudinal members instead of a single serpentine or sinuous member. The frame 1072 comprises a plastically deformable material, an elastically deformable material, or a combination thereof. In embodiments comprising a plastically deformable material, the internal retractor 1070 is reshapeable or adjustable on deployment.

Figure 10B:
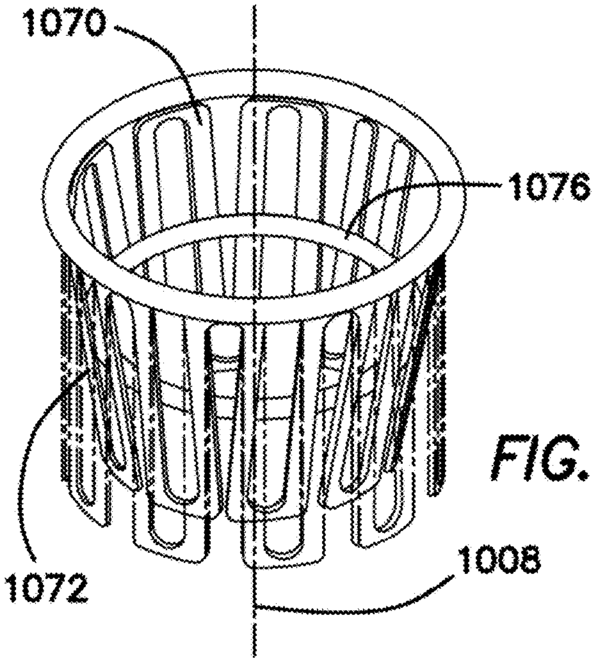
FIG. 10B is a perspective view of the embodiment of FIG. 10A in the undeployed state.
Figure 10C:
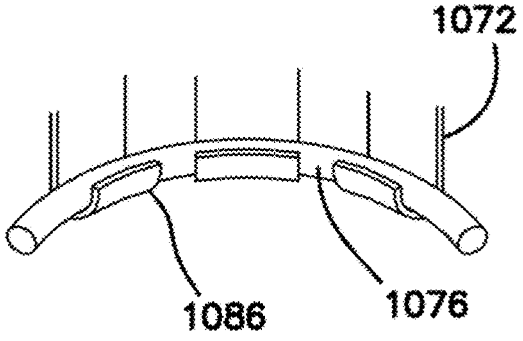
FIG. 10C shows a distal support member engaging the distal end of the internal retractor of FIG. 10A when deployed.

The illustrated embodiment further comprises a distal support member 1076 disposed at a distal end of the internal retractor 1070. As illustrated in FIG. 10B in an undeployed state, the internal retractor 1070 is conical. In deploying the internal retractor 1070, the distal support member 1076 is advanced along the access channel 1008 until it engages a distal end of the frame 1072, for example in a set of hooks 1086, as shown in FIG. 10C.

Some embodiments of the internal retractor 1070 comprise a cover or dam portion (not illustrated). Some embodiments are openable, for example, by cutting the distal support member 1076, if present, or portions of the frame 1072, which permits additional adjustability.

Figure 11:
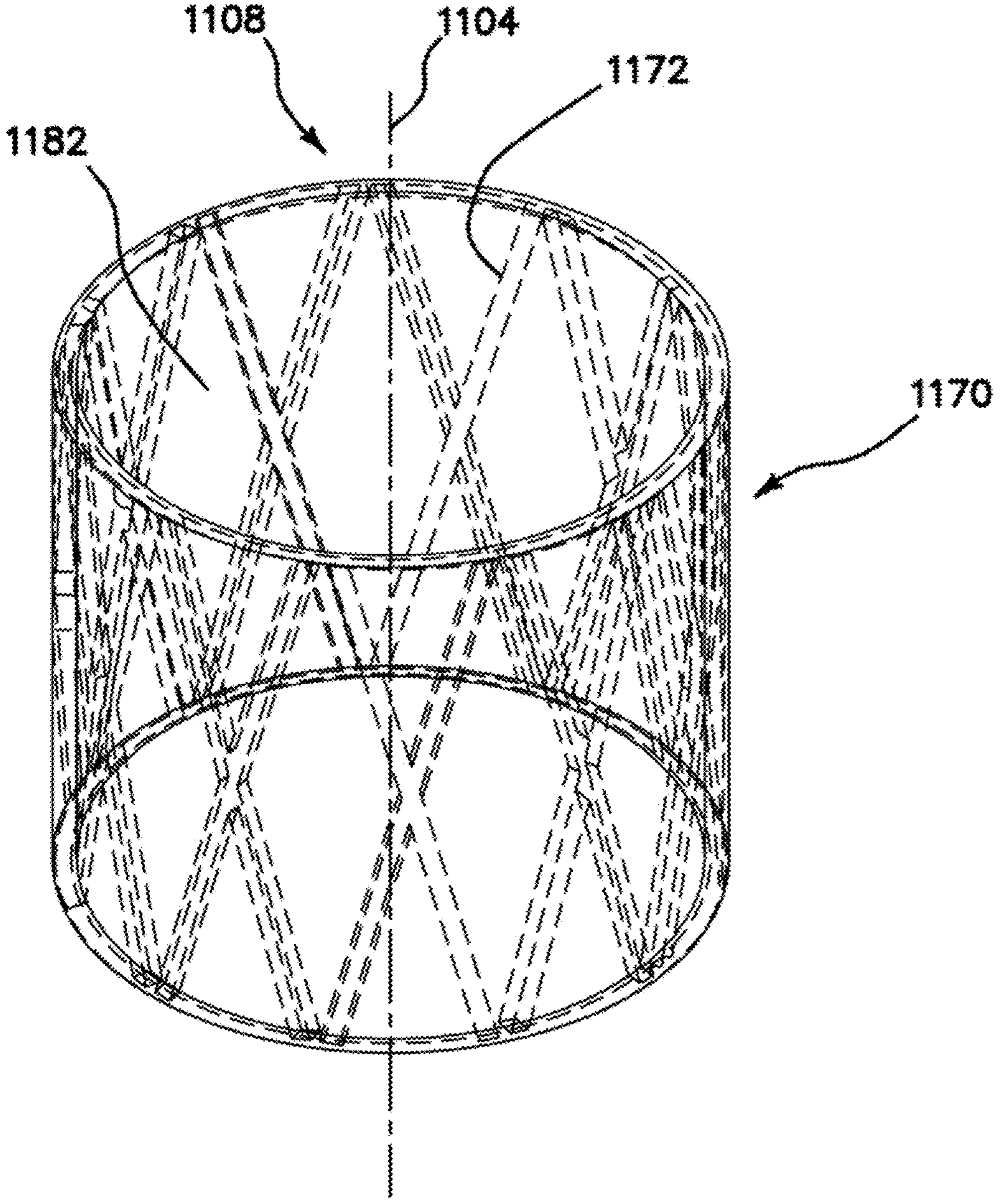
FIG. 11 is a perspective view of another embodiment of an internal retractor comprising a lattice frame defining a tube.

FIG. 11 is a perspective view of another embodiment of an internal retractor 1170, which is similar to the embodiments described above. The internal retractor 1170 is integrated with, couplable with, used with, or used independently of a wound retractor, as discussed above. The illustrated embodiment of the internal retractor 1170 comprises a longitudinal axis 1106, an access channel 1108, and a lattice frame 1172 defining a hollow cylinder or tube. In other embodiments, the frame 1172 defines a different shape, for example, frustoconical or an elliptical cylinder. The lattice frame 1172 defines a plurality of voids or openings 1182 in the cylindrical surface, which permit a user to compress the frame 1172 radially, for example, when inserting the internal retractor 1170. In the illustrated embodiment, the frame 1172 comprises a diamond lattice. In other embodiments, the frame 1172 comprises a different lattice, for example, a hexagonal lattice. The frame 1172 comprises a plastically deformable material, an elastically deformable material, or a combination thereof. In embodiments comprising a plastically deformable material, the internal retractor 1170 is reshapeable or adjustable on deployment.

In the illustrated embodiment, the internal retractor 1170 further comprises a cover or dam portion 1174, as discussed above. Other embodiments do not comprise a cover or dam portion. Some embodiments are openable, for example, by cutting portions of the frame 1172, which permits additional adjustability.

Figure 12:
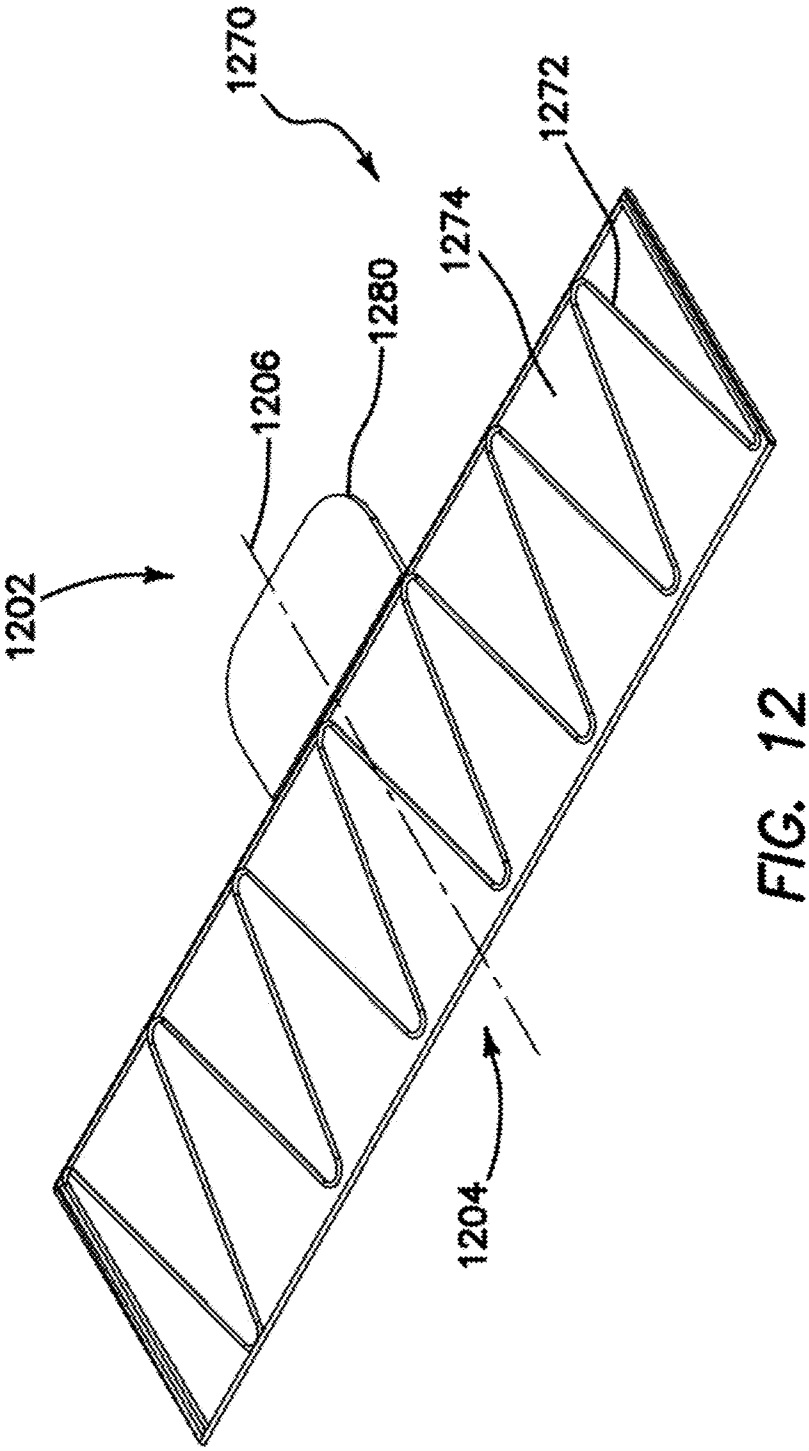
FIG. 12 is a perspective view of another embodiment an internal retractor comprising a planar, deformable frame.

FIG. 12 is a perspective view of another embodiment of an internal retractor 1270, which is similar to the embodiments described above. The internal retractor 1270 is integrated with, couplable with, used with, or used independently of a wound retractor, as discussed above. The illustrated embodiment of the internal retractor 1270 comprises a longitudinal axis 1206 extending between a proximal end 1202 and a distal end 1204, a deformable frame 1272, and a cover or dam portion 1274. The illustrated embodiment also comprises a connection feature 1280, which permits coupling the internal retractor 1270 to a wound retractor, as discussed above. In the illustrated embodiment, the frame 1272 defines a generally rectangular internal retractor 1270. In other embodiments, the frame 1272 defines a different shape, for example, trapezoidal or rhomboidal. The frame 1272 is serpentine in the illustrated embodiment. In other embodiments, the frame 1272 has a different structure, for example, a lattice, a mesh, a solid sheet, a perforated sheet, or a combination of structures. The frame 1272 comprises a plastically deformable material, an elastically deformable material, or a combination thereof. In embodiments comprising a plastically deformable material, the internal retractor 1270 is reshapeable or adjustable on deployment.

In the illustrated embodiment, the internal retractor 1270 further comprises a cover or dam portion 1274, as discussed above. Other embodiments do not comprise a cover or dam portion. Some embodiments are reshapeable, for example, by cutting portions of the frame 1272 and/or cover 1274, which permits additional adjustability.

FIG. 13A illustrates a side view another embodiment of a surgical access device 1300 that is generally similar to the embodiments described above. The surgical access device 1300 comprises a longitudinal axis 1306 extending from a proximal end 1302 to a distal end 1304, an access channel 1308 extending through the device 1300, a wound retractor 1350 disposed at the proximal end 1302 and an internal retractor 1370. The wound retractor 1350 is generally similar to the embodiments of the wound retractor described above, and comprises an outer ring 1352, an inner ring 1354, and a flexible sheath 1356. Embodiments of the internal retractor 1370 are integrated, preattached, or user attached to the wound retractor 1350, or used without coupling to a wound retractor, as discussed above.

As best seen in the detailed view in FIG. 12B, the internal retractor comprises a body 1372 comprising a groove 1380 extending at least partially along a proximal edge thereof, which is dimensioned to receive the inner ring 1354 of the wound retractor 1350 therein. The body 1372 comprises a plastically deformable material, an elastically deformable material, or a combination thereof. In embodiments comprising a plastically deformable material, the body 1372 is reshapeable or adjustable on deployment. In some embodiments, the body 1372 is tubular and dimensioned to the diameter of the inner ring 1354. In other embodiments, the body 1372 is supplied as an elongate strip. In either case, some embodiments of the body 1372 may be trimmed as desired.

In the illustrated embodiment, a connection feature 1388 extends at least partially along the distal edge of the body 1372. As best seen in the perspective view in FIG. 13C, the connection feature 1388 of the body 1372 couples to an extender 1390, which comprises a complementary connector 1392*a* extending at least partially along a proximal edge of the extender 1390. In the illustrated embodiment, the connection feature 1388 and the complementary connector 1392*a* are self-complementary, that is, have the same shape. As with the body 1372, the extender 1390 comprises an elastically deformable material, plastically deformable material, or a combination thereof. In the illustrated embodiment, the extender 1390 further comprises a second complementary connector 1392*b* disposed along at least a portion of a distal edge of the extender 1390, which permits a user to add as many extenders 1390 as desired. Consequently, in the illustrated embodiment, the internal retractor 1370 comprises the body 1372 and any number of extenders 1390 desired.

In other embodiments, the connection feature 1388 has the same cross-sectional shape as the inner ring 1354 of the wound retractor 1350. Consequently, the body 1372 is also an extender in these embodiments.

Figure 14:
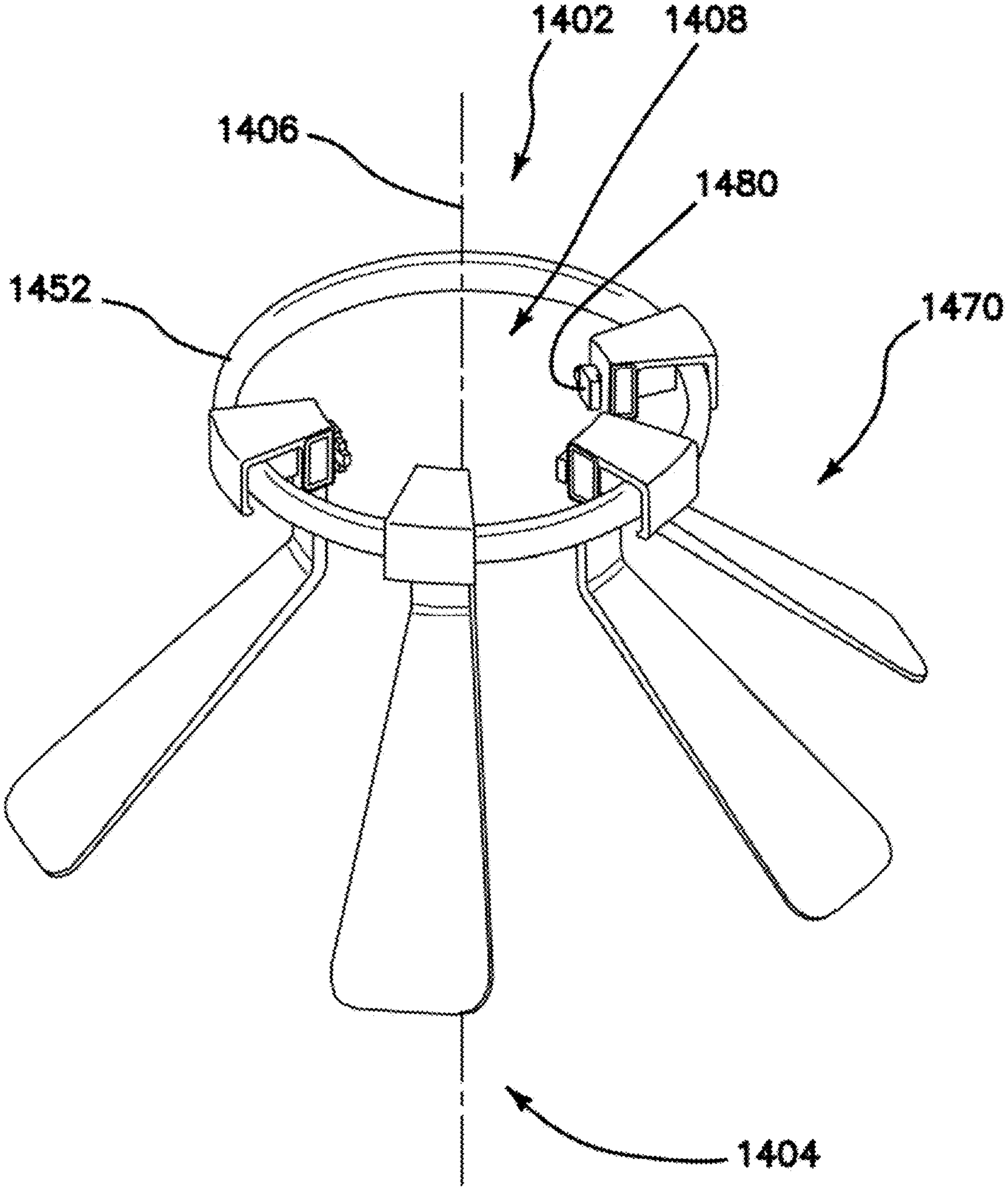
FIG. 14 is a perspective view of another embodiment an internal retractor comprising a plurality of elongate, shapeable members.

FIG. 14 is a perspective view of another embodiment of an internal retractor 1470, which is similar to the embodiments described above. The illustrated embodiment of the internal retractor 1470 comprises a longitudinal axis 1406 extending between a proximal end 1402 and a distal end 1404, an access channel 1408, and a plurality of shapeable members 1472. The shapeable members are similar to the shapeable members 272 described above, except that the shapeable members 1472 of the illustrated embodiment are coupled to an outer ring 1452 of a wound retractor rather than an inner ring.

In the illustrated embodiment, the proximal end of each shapeable member 1472 comprises a connection feature 1480 that couples the shapeable member 1472 to the outer ring 1452. The illustrated configuration permits a user to determine the number and spacing of shapeable members 1472 used in any particular situation. In one embodiment, the user inserts a distal end of the shapeable member 1472 through the access channel 1408, then couples the shapeable member 1472 to the outer ring 1452.

In other embodiments, one or more shapeable members 1472 are deployed as a unit, for example, comprising a common connection feature 1480. In some embodiments comprising a common connection feature 1480, the shapeable members 1472 are substantially longitudinal or convergent when inserted through the access channel 1408, then reshaped after coupling to the outer ring 1452.

Figure 15:
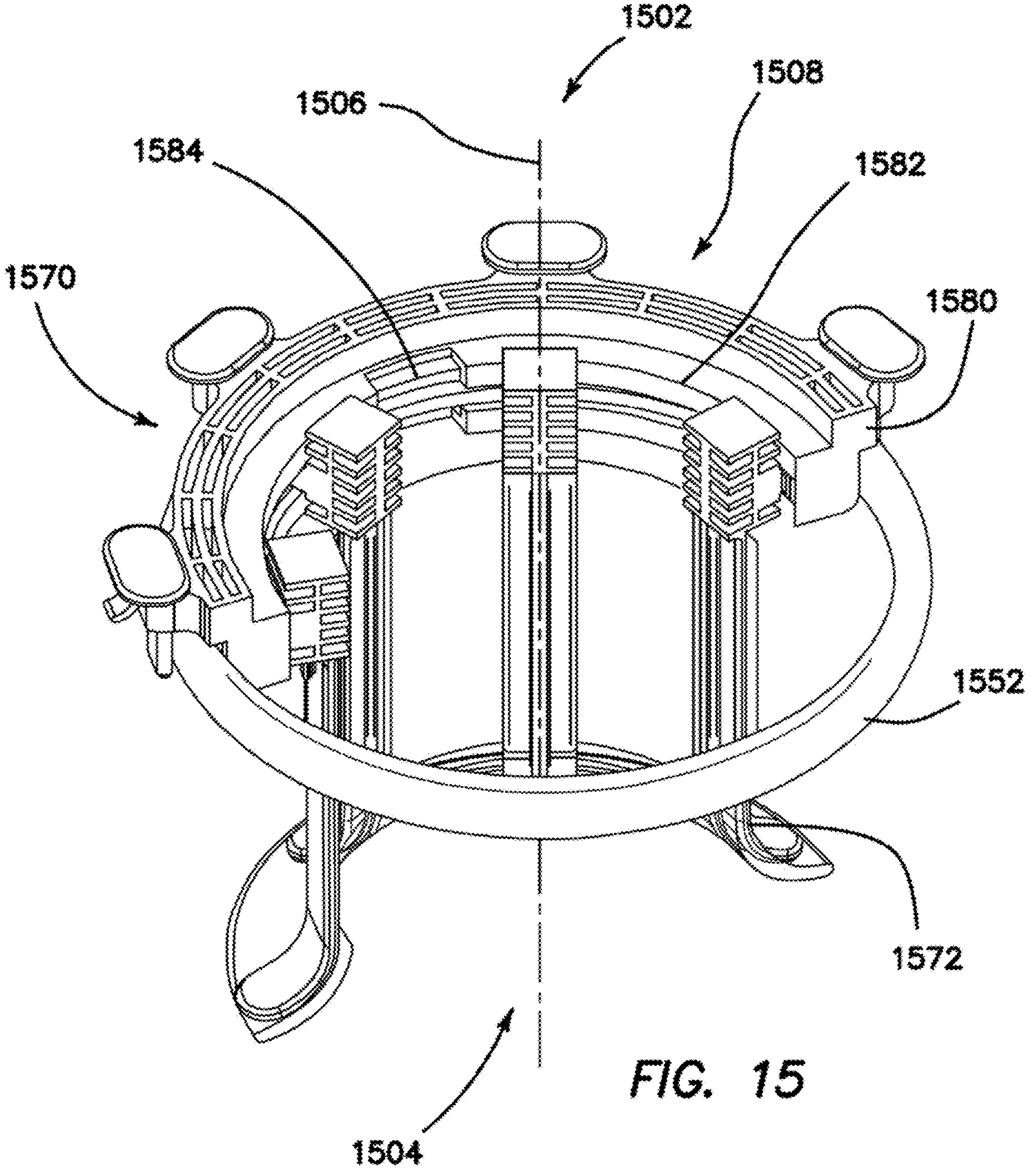
FIG. 15 is a perspective view of another embodiment an internal retractor comprising a plurality of elongate, shapeable members.

FIG. 15 is a perspective view of another embodiment of an internal retractor 1570, which is similar to the embodiments described above. The illustrated embodiment of the internal retractor 1570 comprises a longitudinal axis 1506 extending between a proximal end 1502 and a distal end 1504, an access channel 1508, and a plurality of shapeable members 1572. The shapeable members are similar to the shapeable members 272 and described above, except that the shapeable members 1572 of the illustrated embodiment are coupled to an outer ring 1552 of a wound retractor rather than an inner ring.

In the illustrated embodiment, an arcuate base 1580 releasably mates with the outer ring 1552. In other embodiments, the connection feature has a different arc length, for example, a full circle. The base 1580 comprises a connector 1582 that couples to the shapeable members 1572. In the illustrated embodiment, the connector 1582 comprises a T-track into which is received a complementary portion disposed at a proximal end of each shapeable member 1472. Those skilled in the art will understand that other embodiments use connectors with other configurations, for example, rails, tracks, holes, posts, and the like. In the illustrated embodiment, the connector 1582 is disposed along an inner surface of the base. In other embodiments, the connector is disposed on another surface, for example, a proximal face, an outer face, or a face at another angle to the longitudinal axis 1506. The shapeable members 1572 are slidable along the T-track. The T-track comprises a gap 1584 dimensioned to permit a user to insert or remove shapeable member therethrough. The illustrated configuration permits a user to determine the number and spacing of shapeable members 1572 used in any particular situation. In one embodiment, the user couples the base 1580 to the outer ring 1552, inserts a distal end of the shapeable member 1572 through the access channel 1508, aligns the shapeable member with the gap 1584, then couples the shapeable member 1572 to the connector 1582.

Figure 16A:
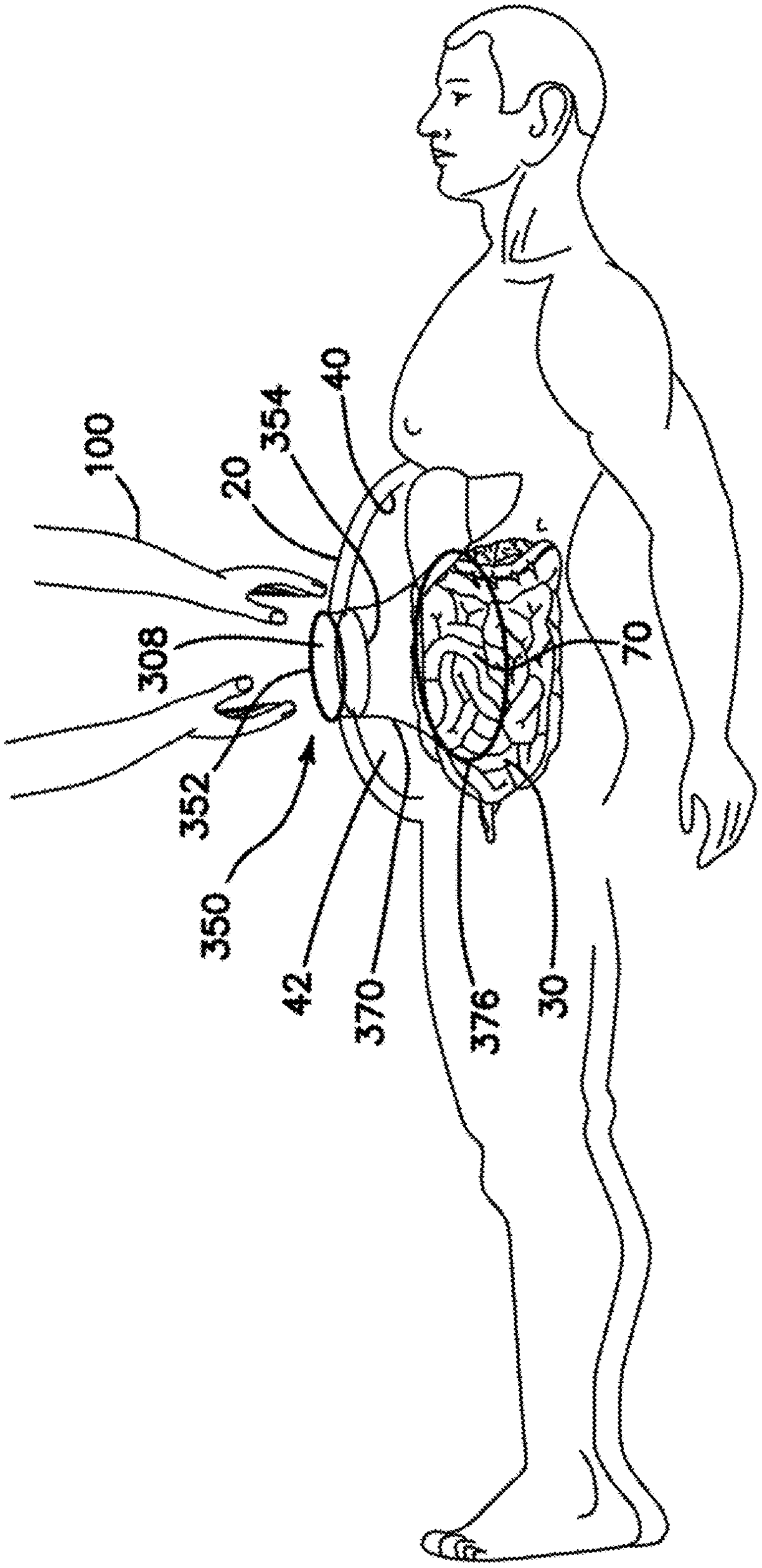
FIG. 16A is a partial side cross section of a patient prior to deploying an internal retractor in the abdomen.
Figure 16B:
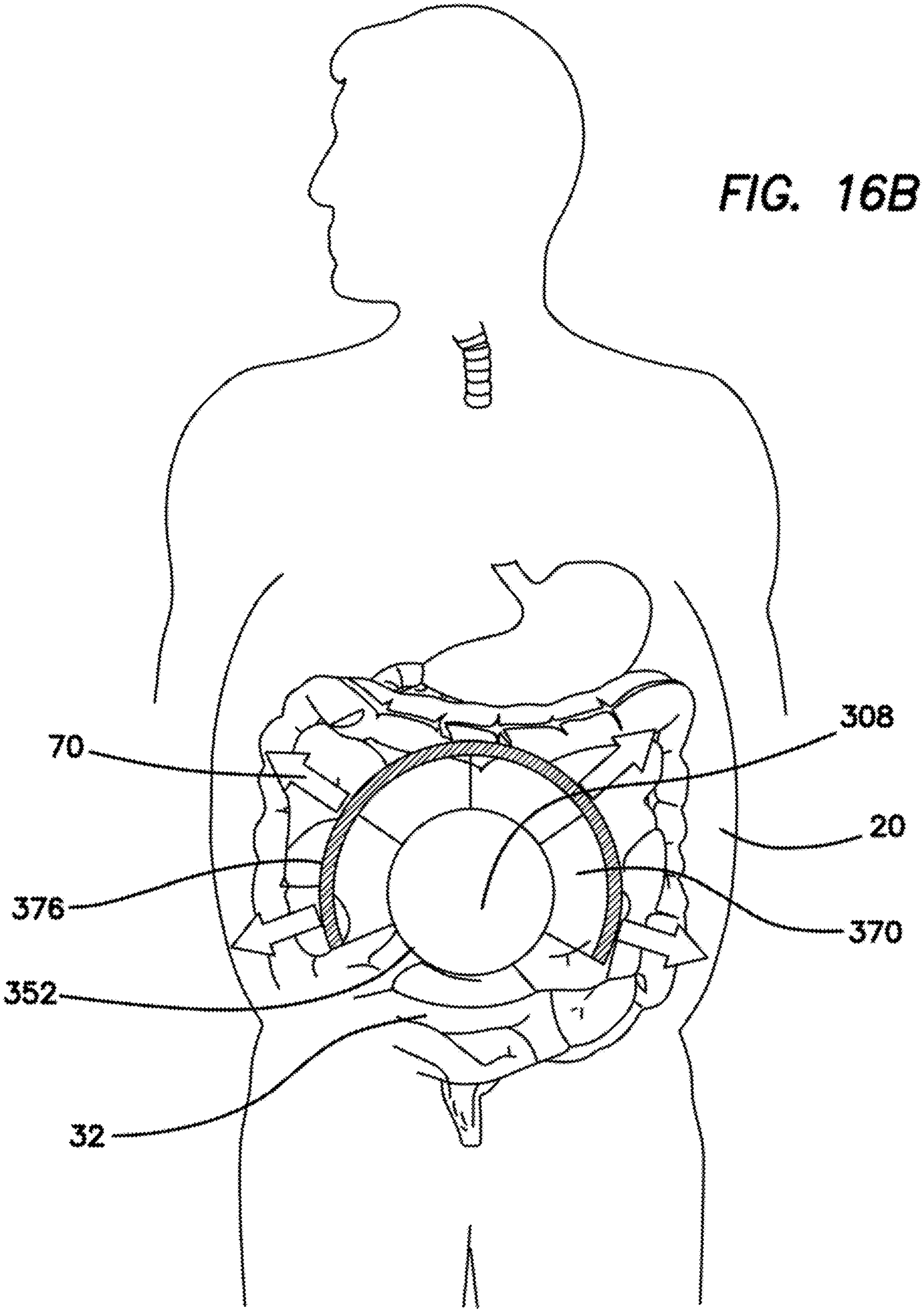
FIG. 16B is a partial front cross section and FIG. 16C is a partial side cross section of a patient in which an internal retractor has been deployed in the abdomen.
Figure 16C:
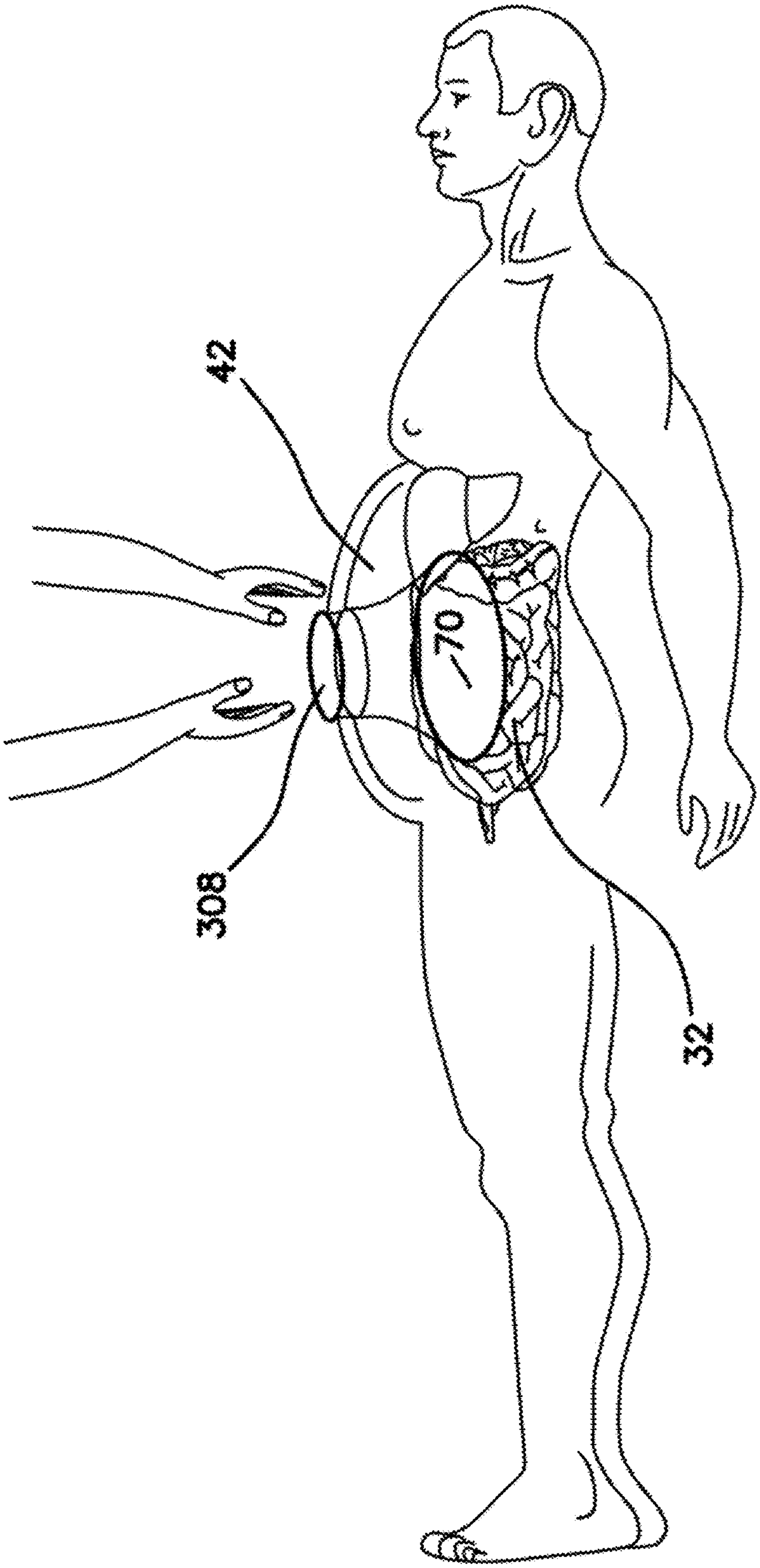

An embodiment of a method for using a surgical access device in abdominal surgery is schematically illustrated in FIGS. 16A-16C and described with reference to the embodiment of the access device 300 illustrated in FIG. 3, although one skilled in the art will understand that the method is also applicable to all of the embodiments of the access device described herein. FIG. 16A is a side, partial cross section of a patient in which a wound retractor 350 has been placed through a body wall 40 and into a body cavity 42, which is an abdominal cavity in this case. The inner ring 354 and internal retractor 370 are first inserted through an incision in the body wall 40 into the body cavity 42. The outer ring 352 is then inverted through or rotated around itself, thereby winding the tubular sheath 356 around the outer ring 352, thereby retracting the incision. In some embodiments, the outer ring 352 of the proximal portion is easily invertible in a snap-over motion, which provides a neutral position that resists rotation under tension generated in the retraction process. The tension secures the retractor 350 to the body wall 40.

In the illustrated embodiment, the abdominal cavity 42 is inflated with gas, thereby facilitating access to internal structures 30. In some embodiments, a cap or cover (not illustrated) is secured to the proximal portion of the retractor 350, thereby creating a substantially gas-tight closure to the body cavity 42, after which, the body cavity 42 is inflated or insufflated, for example, with $CO_2$ gas.

The internal retractor 370 is then deployed as desired within the body cavity 42, thereby retracting or retaining internal structures during the surgical procedure. FIG. 16A illustrates the surgical site 70 before deploying the internal retractor 370. For example, in the illustrated procedure, the position of abdominal content 30 is adjusted for an operation below the small intestine 32. FIG. 16B illustrates a front partial cross section and FIG. 16C illustrates a side partial cross section of a retention pattern in which the internal retractor 370 holds the small intestine 32 away from the operative site 70.

In the illustrated embodiment, deploying the internal retractor 370 comprises positioning the peripheral ring 376 of the internal retractor 370, and inflating the inflatable supporting member 372 to a desire state of retention or retraction of the internal structures 30. The inflated internal retractor 370 dams or walls-off loose structures from the operative site 70. In inserting the access device 300, as well as in deploying the internal retractor 370, the internal retractor 370 is manipulated manually and/or with an instrument. For example, in some embodiments, the access device 300 is dimensioned and configured for access to the body cavity 22 by a surgeon's hand 100 through the orifice access channel 608 of the access device 300. Other embodiments use a smaller access device 300 that is sized and configured to accept surgical instruments, such as laparoscopic tools, therethrough, but not a hand. In some cases, using a single, smaller device 300 limits the number of incisions needed in a laparoscopic procedure. Those skilled in the art will understand that the particular deployment procedure for the extendable member differs for each embodiment described above.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A surgical access device comprising:

a wound retractor comprising an outer ring, an inner ring, and a tubular sheath connected to the outer ring and the inner ring;

an internal retractor comprising a longitudinal axis extending between a proximal end and a distal end, an access channel, and a plurality of shapeable members coupled to the outer ring of the wound retractor;

an arcuate base releasably mating with the outer ring, the plurality of shapeable members coupled to the arcuate base;

wherein each of the plurality of shapeable members are slidable along an inner surface of the arcuate base.

2. The surgical access device of claim 1, wherein the plurality of shapeable members are spaced from one another.

3. The surgical access device of claim 2, wherein spacing between the plurality of shapeable members is adjustable.

4. The surgical access device of claim 3, wherein a distal end of each of the plurality of shapeable members is insertable through the access channel.

5. The surgical access device of claim 4, wherein the plurality of shapeable members extend longitudinally when inserted through the access channel and are reshapeable after coupling to the outer ring.

6. The surgical access device of claim 1, further comprising a connector coupling the plurality of shapeable members to the arcuate base.

7. The surgical access device of claim 6, wherein the connector comprises a T-track configured to receive a complementary portion disposed at a proximal end of each of the plurality of shapeable members.

8. The surgical access device of claim 7, wherein the T-track comprises a gap configured to permit removable of a shapeable member from the plurality of shapeable members coupled to the outer ring.

9. The surgical access device claim 1, wherein at least one of the plurality of shapeable members are removable from the arcuate base.

10. The surgical access device of claim 1, wherein the outer ring of the wound retractor is rotatable around an annular axis thereof, thereby permitting adjustment of an effective length of the tubular sheath between the inner ring and the outer ring.

11. The surgical access device of claim 10, wherein the internal retractor is user coupled to the wound retractor in the operative state.

12. A method for defining a surgical field in a body cavity comprising:

inserting the inner ring of the wound retractor of the surgical access device of claim 1 through an opening in a body wall and into a body cavity;

retracting the opening in the body wall; and deploying the internal retractor within the body cavity and defining a surgical field.

13. A surgical access device comprising:

a wound retractor comprising an outer ring, an inner ring, and a tubular sheath connected to the outer ring and the inner ring; and an internal retractor comprising a longitudinal axis extending between a proximal end and a distal end, an access channel, and a plurality of shapeable members coupled to the outer ring of the wound retractor;

wherein the internal retractor comprises a body comprising a groove extending along at least a proximal edge of the body, the groove configured to receive the inner ring of the wound retractor and an extender coupled to the body;

wherein the body further comprises a connection feature disposed along at least a portion of a distal edge of the body, wherein the connection feature is couplable with the extender comprising a complementary connector disposed along at least a portion of a proximal edge of the extender.

14. The surgical access device of claim 13, wherein the extender is a first extender and further comprising a second extender couplable with a distal edge of the first extender.

* * * * *